(12) United States Patent
Hile

(10) Patent No.: US 8,754,307 B2
(45) Date of Patent: Jun. 17, 2014

(54) VARIETY CORN LINE NPJC6794

(75) Inventor: Glenn Cornell Hile, Monroeville, IN (US)

(73) Assignee: Syngenta Particpations AG, Basel (CH)

( * ) Notice: Subject to any disclaimer, the term of this patent is extended or adjusted under 35 U.S.C. 154(b) by 132 days.

(21) Appl. No.: 13/400,149

(22) Filed: Feb. 20, 2012

(65) Prior Publication Data

US 2012/0222154 A1 Aug. 30, 2012

Related U.S. Application Data

(60) Provisional application No. 61/463,905, filed on Feb. 24, 2011.

(51) Int. Cl.
- *A01H 5/00* (2006.01)
- *A01H 5/10* (2006.01)
- *A01H 1/00* (2006.01)
- *C12N 15/82* (2006.01)

(52) U.S. Cl.
USPC ........ 800/320.1; 800/260; 800/275; 800/300; 800/300.1; 800/301; 800/278

(58) Field of Classification Search
None
See application file for complete search history.

(56) References Cited

U.S. PATENT DOCUMENTS

| | | | |
|---|---|---|---|
| 5,723,735 | A | 3/1998 | Matson |
| 5,780,705 | A | 7/1998 | Witherspoon et al. |
| 5,792,905 | A | 8/1998 | Henson |
| 6,483,014 | B1 | 11/2002 | Mies |
| 7,807,889 | B2 * | 10/2010 | Graham ..................... 800/320.1 |

OTHER PUBLICATIONS

PVP Certificate No. 9600035 issued Aug. 29, 1997.
PVP Certificate No. 9600268 issued Jun. 30, 1999.
PVP Application No. 201100278 filed Feb. 23, 2011.

* cited by examiner

*Primary Examiner* — Stuart F Baum
(74) *Attorney, Agent, or Firm* — Dale Skalla

(57) ABSTRACT

The present invention provides an inbred corn line designated NPJC6794, methods for producing a corn plant by crossing plants of the inbred line NPJC6794 with plants of another corn plant. The invention further encompasses all parts of inbred corn line NPJC6794, including culturable cells. Additionally provided herein are methods for introducing transgenes into inbred corn line NPJC6794, and plants produced according to these methods.

18 Claims, No Drawings

VARIETY CORN LINE NPJC6794

REFERENCE TO RELATED APPLICATIONS

This application claims the priority benefit under Title 35, United States Code 119(e) of U.S. Provisional Patent Application No. 61/463,905 filed Feb. 24, 2011.

FIELD OF THE INVENTION

This invention is in the field of corn breeding. Specifically, the present invention provides a maize plant and its seed designated NPJC6794, as well as derivatives and hybrids thereof.

BACKGROUND OF THE INVENTION

Maize (or corn; *Zea mays* L.) plant breeding is a process to develop improved maize germplasm in an inbred or hybrid plant. Maize plants can be self-pollinating or cross pollinating. Self pollination for several generations produces homozygosity at almost all gene loci, forming a uniform population of true breeding progeny, known as inbreds. Hybrids are developed by crossing two homozygous inbreds to produce heterozygous gene loci in hybrid plants and seeds. In this process, the inbred is emasculated and the pollen from the other inbred pollinates the emasculated inbred. Emasculation of the inbred can be done by chemical treatment of the plant, detasseling the seed parent, or the parent inbred can comprise a male sterility trait or transgene imparting sterility, eliminating the need for detasseling. This emasculated inbred, often referred to as the female, produces the hybrid seed, F1. The hybrid seed that is produced is heterozygous. However, the grain produced by a plant grown from F1 hybrid seed is referred to as F2 grain. F2 grain which is a plant part produced on the F1 plant will comprise segregating maize germplasm, even though the hybrid plant is heterozygous.

Such heterozygosity in hybrids results in robust and vigorous plants. Inbred plants on the other hand are mostly homozygous, rendering them less vigorous. Inbred seed can be difficult to produce due to such decreased vigor. However, when two inbred lines are crossed, the resulting hybrid plant shows greatly increased vigor and seed yield compared to open pollinated, segregating maize plants. An important consequence of the homozygousity and homogeneity of inbred maize lines is that all hybrid seed and plants produced from any cross of two such lines will be the same. Thus the use of inbreds allows for the production of hybrid seed that can be readily reproduced.

There are numerous stages in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The aim is to combine in a single variety an improved combination of desirable traits from the parental germplasm. These important traits may include, for example, higher yield, resistance to diseases, fungus, bacteria and insects, better stems and roots, tolerance to drought and heat, improved nutritional quality, and better agronomic characteristics.

Choice of breeding methods depends on the mode of plant reproduction, the heritability of the trait(s) being improved, and the type of cultivar used commercially (e.g., F1 hybrid cultivar, pure line cultivar, etc.). For highly heritable traits, a choice of superior individual plants evaluated at a single location may be effective, whereas for traits with low heritability, selection can be based on mean values obtained from replicated evaluations of families of related plants. Popular selection methods commonly include pedigree selection, modified pedigree selection, mass selection, and recurrent selection.

The complexity of inheritance influences the choice of breeding method. Backcross breeding is used to transfer one or a few favorable genes for a highly heritable trait into a desirable cultivar. This approach has been used extensively for breeding disease-resistant cultivars and introducing transgenic events into maize germplasm. Thus, backcross breeding is useful for transferring genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Each breeding program generally includes a periodic, objective evaluation of the efficiency of the breeding procedure. Evaluation criteria vary depending on the goals and objectives, but should include gain from selection per year based on comparisons to an appropriate standard, overall value of the advanced breeding lines, and number of successful cultivars produced per unit of input (e.g., per year, per dollar expended, etc.).

The ultimate objective of commercial corn breeding programs is to produce high yield, agronomically sound plants that perform well in particular regions of the U.S. Corn Belt, such as a plant of this invention.

SUMMARY OF THE INVENTION

In one aspect, the present invention provides a seed of the maize inbred plant NPJC6794, representative seed of said plant having been deposited.

In a further aspect, the present invention provides a maize inbred plant NPJC6794, representative seed of said NPJC6794 plant having been deposited. And the seed wherein said seed further comprises a mutant or transgenic gene that confers a characteristic selected from the group consisting of herbicide resistance, insect resistance and disease resistance male sterility, altered amylase, site-specific recombination, abiotic stress tolerance, altered phosphorus, altered antioxidants, altered fatty acids, altered amino acids, and altered carbohydrates.

Further provided is a plant part of the plant of this invention, which includes but is not limited to pollen, protoplast, cell, tassel, anther, ovule or seed or grain.

Additional aspects of this invention include a process for producing an F1 hybrid maize seed, said process comprising crossing a plant of maize inbred plant NPJC6794 with a different maize plant and harvesting the resultant F1 hybrid maize seed. A maize plant or plant part produced by growing the F1 hybrid maize seed is also provided herein. The present invention also provides a maize seed produced by crossing the plant of this invention with a different maize plant.

The present invention further provides an F1 hybrid maize seed comprising an inbred maize plant cell of inbred maize plant NPJC6794.

A method is also provided for producing maize seed comprising growing the plant of this invention until seed is produced and harvesting the seed, wherein the harvested seed is inbred or hybrid or haploid seed. And a method of producing seed, comprising crossing the plant of the invention with itself or a second maize plant. Seed produced by this method is also provided herein. Hybrid seed produced by crossing the invention with a second distinct corn plant and the plant and plant parts on this hybrid plant grown from the hybrid seed.

Additional aspects of this invention include a process of introducing a desired heritable trait into maize inbred plant NPJC6794, comprising: (a) crossing NPJC6794 plants grown from NPJC6794 seed with plants of another maize plant that comprise a desired trait to produce hybrid progeny plants, (b) selecting hybrid progeny plants that have the desired trait to produce selected hybrid progeny plants; (c) crossing the selected progeny plants with the NPJC6794 plants to produce backcross progeny plants; (d) selecting for backcross progeny plants that have the desired trait to produce selected backcross progeny plants; and (e) repeating as necessary backcrossing and step (d) to produce backcross progeny plants of subsequent generations that comprise the desired trait and all of the physiological and morphological characteristics of maize inbred plant NPJC6794 when grown in the same environmental conditions. In some embodiments of this invention, the desired trait can be, but is not limited to, waxy starch, male sterility, herbicide resistance, nematode resistance, modified amylase, altered starch, thermotolerant amylase, insect resistance, modified carbohydrate metabolism, protein metabolism, fatty acid metabolism, bacterial resistance, disease resistance, fungal disease resistance, viral disease resistance, or any combination thereof. A plant produced by this process is also provided herein. Or a conversion of maize variety X, wherein representative seed of said maize variety X comprising at least one new trait wherein said conversions had the morphological and physiological traits of maize and said trait confers a characteristic selected from the group consisting of altered amylase, abiotic stress and biotic stress tolerance, herbicide, insect, fungal, bacterial and disease resistance.

Furthermore, the present invention provides a maize plant having all the physiological and morphological characteristics of inbred plant NPJC6794, wherein a sample of the seed of inbred plant NPJC6794 was deposited under ATCC Accession Number PTA-12400. The maize plant of this invention can comprise a genome which further comprises at least one transgene and/or the maize plant can exhibit a trait conferred by a transgene. In some embodiments of this invention, the transgene can confer a trait of herbicide resistance or tolerance; insect resistance or tolerance; resistance or tolerance to bacterial, fungal, nematode or viral disease; waxy starch; altered starch, male sterility or restoration of male fertility, modified carbohydrate metabolism, modified fatty acid metabolism, or any combination thereof.

Additionally provided herein is a method of producing a maize plant derived from the inbred plant NPJC6794, comprising the steps of: (a) growing a progeny plant wherein the inbred plant is one parent of the progeny; (b) crossing the progeny plant with itself or a different plant to produce a seed of a progeny plant of a subsequent generation; (c) growing a progeny plant of a subsequent generation from said seed and crossing the progeny plant of a subsequent generation with itself or a different plant; and (d) repeating steps (b) and (c) for an additional 0-5 generations to produce a maize plant derived from the inbred plant NPJC6794.

Another aspect of this invention includes a method for developing a maize plant in a maize plant breeding program, comprising applying plant breeding techniques comprising recurrent selection, backcrossing, pedigree breeding, marker enhanced selection, haploid/dihaploid production, or transformation to the maize plant of this invention, or its parts, wherein application of said techniques results in development of a maize plant.

Furthermore, the present invention provides a method of producing a commodity plant product comprising growing the plant from the seed of this invention or a part thereof and producing said commodity plant product, wherein said commodity plant product can be, but is not limited to a protein concentrate, a protein isolate, starch, meal, flour, oil therefrom, or any combination thereof.

A method is also provided of producing a treated seed of this invention, comprising obtaining the seed of NPJC6794 and treating said seed.

DETAILED DESCRIPTION OF THE INVENTION

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

In the description and examples that follow, a number of terms are used. In order to provide a clear and consistent understanding of the specifications and claims, including the scope to be given such terms, the following definitions are provided.

Definitions of Plant Characteristics

Early Season Trait Codes

Emergence Rating (EMRGR): Recorded when 50% of the plots in the trial are at V1 (1 leaf collar) growth stage. Various responses include, but are not limited to, (1) All plants have emerged and are uniform in size; (2) All plants have emerged but are not completely uniform; (3) Most plants have emerged with some just beginning to break the soil surface, noticeable lack of uniformity; (4) Less than 50% of the plants have emerged, and lack of uniformity is very noticeable; or (5) A few plants have emerged but most remain under the soil surface.

Seedling Growth (SVGRR or Vigor): Recorded between V3 and V5 (3-5 leaf stage) giving greatest weight to seedling plant size and secondary weight to uniform growth. Various responses include, but are not limited to, (1) Large plant size and uniform growth; (2) Acceptable plant size and uniform growth; (3) Acceptable plant size and might be a little non-uniform; (4) Weak looking plants and non-uniform growth; or (5) Small plants with poor uniformity.

Purpling (PRPLR): Emergence and/or early growth rating. Purpling is more pronounced on the under sides of leaf blades especially on midribs. Various responses include, but are not limited to, (1) No plants showing purple color; (2) 30% plants showing purple color; (3) 50% plants showing purple color; (4) 70% plants showing purple color; or (5) 90+% plants showing purple color.

Herbicide Injury (HRBDR): List the herbicide type that is being rated. Then rate each hybrid/variety injury as indicated below. (1) No apparent reduction in biomass or other injury symptoms; (2) Moderate reduction in biomass with some signs of sensitivity; (3) Severe reduction in biomass with some mortality.

Mid-Season Trait Codes

Heat Units to 50% Silk (HU5SN): Recorded the day when 50% of all plants within a plot show 2 cm or more silk protruding from the ear. Converted days to accumulated heat units from planting.

Heat units to 50% Pollen Shed (HUPSN): Recorded the day when 50% of all plants within a plot are shedding pollen. Converted days to accumulated heat units from planting.

Plant Height (PLHTN): After pollination, recorded average plant height of each plot. Measured from ground to base of leaf node.

Plant Ear Height (ERHTN) in cm: After pollination, record average ear height of each plot. Measure from ground to base of ear node (shank).

Root Lodging Early % (ERTLP): Early root lodging occurs up to about two weeks after flowering and usually involves goosenecking. The number of root lodged plants are counted and converted to a percentage.

Shed Duration (Shed Duration): Sum of daily heat units for days when plants in the plot are actively shedding pollen.

Foliar Disease (LFDSR): Foliar disease ratings taken one month before harvest and through harvest. The predominant disease should be listed in the trial information and individual hybrid ratings should be given. Various responses include, but are not limited to, (1) No lesions to two lesions per leaf; (2) A few scattered lesions on the leaf. About five to ten percent of the leaf surface is affected; (3) A moderate number of lesions are on the leaf. About 15 to 20 percent of the leaf surface is affected; (4) abundant lesions are on the leaf. About 30 to 40 percent of the leaf surface is affected; or (5) Highly abundant lesions (>50 percent) on the leaf. Lesions are highly coalesced. Plants may be prematurely killed. Alternatively, the response to diseases can also be rated as: R=Resistant=1 to 2 rating; MR=Moderately Resistant=3 to 4 rating; MS=Moderately Susceptible=5 to 6 rating; S=Susceptible=7 to 9 rating Preharvest Trait Codes Heat units to Black Layer (HUBLN): The day when 50% of all plants within a plot reach the black layer stage is recorded. Convert days to accumulated heat units from planting.

Harvest Population (HAVPN): The number of plants in yield rows, excluding tillers, in each plot is counted.

Barren Plants (BRRNP): The number of plants in yield rows having no ears and/or abnormal ears with less than 50 kernels is counted.

Dropped Ears (DROPP): The numbers of ears lying on the ground in yield rows are counted.

Stalk Lodging % (STKLP): Stalk lodging will be reported as number of plants broken below the ear without pushing, excluding green snapped plants. The number of broken plants in yield rows is counted and converted to percent.

Root Lodging Late % (LRTLP): Late root lodging can usually start to occur about two weeks after flowering and involves lodging at the base of the plant. Plants leaning at a 30-degree angle or more from the vertical are considered lodged. The number of root lodged plants in yield rows is counted and converted to percent.

Push Test for Stalk and Root Quality on Erect Plants % (PSTSP or PCT Push or % Pushtest): The push test is applied to trials with approximately five percent or less average stalk lodging. Plants are pushed that are not root lodged or broken prior to the push test. Standing next to the plant, the hand is placed at the top ear and pushed to arm's length. Push one of the border rows (four-row small plot) into an adjacent plot border row. The number of plants leaning at a 30-degree angle or more from the vertical, including plants with broken stalks prior to pushing is counted. Plants that have strong rinds that snap rather than bend over easily are not counted. The goal of the push test is to identify stalk rot and stalk lodging potential, NOT ECB injury. Data may be collected for the push test in the following manner:

PUSXN: Push ten plants and enter the number of plants that do not remain upright.

Intactness (INTLR): Responses can include, but are not limited to, (1) Healthy appearance, tops unbroken; (2) 25% of tops broken; or (3) Majority of tops broken Plant Appearance (PLTAR): This is a visual rating based on general plant appearance, taking into account all factors of intactness, pest and disease pressure. Various responses include, but are not limited to, (1) Complete plant with healthy appearance; (2) Plants look okay; or (3) Plants are not acceptable.

Green Snap (GRSNP or PCTGS or % GreenSnap): Count the number of plants in yield rows that snap below the ear due to brittleness associated with high winds.

Stay-green (STGRP): This is an assessment of the ability of a grain hybrid to retain green color as maturity approaches (taken near the time of black-layer formation) and should not be a reflection of hybrid maturity or leaf disease. Record as a percentage of green tissue. This may be listed as a Stay Green Rating instead of a percentage.

Stay Green Rating (STGRR): This is an assessment of the ability of a grain hybrid to retain green color as maturity is approached (taken near the time of black layer formation or if major differences are noted later). This rating should not be a reflection of the hybrid maturity or leaf disease. Ratings are 1-9. (1=best, 9=worst) 1=solid Green Plant 9=no green tissue Ear/Kernel Rots (KRDSR): If ear or kernel rot is present, husk ten consecutive ears in each plot and count the number that have evidence of ear or kernel rot, multiply by 10, and round up to the nearest rating as described below. Identify and record the disease primarily responsible for the rot. The rot response can include but is not limited to (1) No rot, 0% of the ears infected; (2) Up to 10% of the ears infected; (3) 11 to 20% of the ears infected; (4) 21 to 35% of the ears infected; or (5) 36% or more of the ears infected.

Grain Quality (GRQUR): Observations taken on husked ears after black layer stage. The kernel cap integrity and relative amount of soft starch endosperm along the sides of kernels are rated. Grain quality ratings can include but are not limited to (1) Smooth kernel caps and or 10% or less soft starch; (2) Slight kernel wrinkles and or 30% soft starch; (3) Moderate kernel wrinkles and or 70% soft starch; or (4) Severe kernel wrinkled and or 90% or more soft starch.

Preharvest Hybrid Trait Codes

Ear Shape (DESHR): Description of ear shape can include, but is not limited to, (1) Blocky; (2) Semi-blocky; or (3) Slender.

Ear Type (EARFR): Description of ear type can include, but is not limited to, (1) Flex; (2) Semi-flex; or (3) Fixed.

Husk Cover (HSKCR): Description of husk cover can include, but is not limited to, (1) Long; (2) Medium; or (3) Short.

Kernel Depth (KRLNR): Description of kernel depth can include, but is not limited to, (1) Deep; (2) Medium; or (3) Short (shallow).

Shank Length (SHLNR): Description of shank length can include, but is not limited to, (1) Short; (2) Medium; or (3) Long.

Kernel Row Number (KRRWN): The average number of kernel rows on 3 ears.

Cob diameter (COBDR): Cob diameter is to be taken with template. Description of cob diameter can include, but is not limited to, (1) Small; (2) Medium; or (3) Large.

Harvest Trait Codes
  Number of Rows Harvested (NRHAN)
  Plot Width (RWIDN)
  Plot Length (RLENN)
  Yield Lb/Plot (YGSMN): Bushels per acre adjusted to 15.5% moisture.
  Test Weight (TSTWN or TWT): Test weight at harvest in pounds per bushel.
  Moisture % (MST_P): Percent moisture of grain at harvest.
  Adjusted Yield in Bu/A (YBUAN) listing of bushels per acre of harvested seed at standard moisture
  Kernel Type (KRTPN): Description of kernal type can include, but is not limited to, (1) Dent; (2) Flint; (3) Sweet; (4) Flour; (5) Pop; (6) Ornamental; (7) Pipecorn; or (8) Other.
  Endosperm Type (KRTEN): Description of endosperm type can include, but is not limited to, (1) Normal; (2) Amylose (high); (3) Waxy (4) Sweet; (5) Extra sweet; (6) High protein; (7) High lysine; (8) Super sweet; (9) High oil; or (10) Other.
  Sterile Type (MSCT): Description of sterile type can include, but is not limited to, (1) No; If yes, cytoplasm type can include but is not limited to, (2) C-type or (3) S-type if other (4) for example, transgene
  Anthocyanin of Brace Roots (PBRCC): Refers to the presence of color on 60% of the brace roots during pollen shed. The description of the anthocyanin of brace roots can include, but is not limited to, (1) Absent; (2) Faint; (3) Moderate; (4) Dark; (5) Brace Roots not present; (6) Green; (7) Red; or (8) Purple.
  Anther Color (ANTCC): At 50 percent pollen shed observe the color of newly extruded anthers, pollen not yet shed. The description of the anther color can include, but is not limited to, (1) Yellow; (2) Red; (3) Pink; or (4) Purple
  Glume Color (GLMCC): Color of glumes prior to pollen shed. The description of the glume color can include, but is not limited to, (1) Red or (2) Green.
  Silk Color (SLKCC; SLKCN): Taken at a late flowering stage when all plants have fully extruded silk. Silks at least 2" long but still fresh. The description of the silk color can include, but is not limited to, (1) Yellow; (2) Pink; or (3) Red (e.g., Munsell value).
  Kernel Color (KERCC): The main color of the kernel from at least three ears per ear family. The description of the kernel color can include, but is not limited to, (1) Yellow; or (2) White.
  Cob Color (COBCC; COBCC): The main color of the cob after shelling from at least three ears per ear family. The description of the cob color can include, but is not limited to, (1) Red; (2) Pink; or (3) White (e.g., Munsell value).
Additional Definitions Relating to Plant Culture and Plant Characteristics
  Final Number of Plants Per Plot EMRGN
  Region Developed (REGNN): Various response can include, but are not limited to, (1) Northwest; (2) Northcentral; (3) Northeast; (4) Southeast; (5) Southcentral; (6) Southwest; or (7) Other.
  Cross type (CRTYN); The cross types include, but are not limited to, (1) sc 2; (2) dc; (3) 3w; (4) msc; (5) m3w; (6) inbred; (7) rel. line; or (8) Other.
  Days to Emergence (EMERN).
  Percent Root lodging (before anthesis) (ERTLP).
  Percent Brittle snapping (before anthesis) (GRSNP).
  Tassel branch angle (degree) of 2nd primary lateral branch (at anthesis) (TBANN).
  Days to 50% silk in adapted zone (DSAZN).
  Heat units to 90% pollen shed (from emergence) (HU9PN).
  Days from 10% to 90% pollen shed (DA19N).
  Heat units from 10% to 90% pollen shed (HU19N).
  Heat units to 10% pollen shed: (from emergence) (HU1PN)
  Leaf sheath pubescence of second leaf above the ear (at anthesis) 1-9 (1=none) (LSPUR).
  Angle (degree) between stalk and 2nd leaf above the ear (at anthesis) (ANGBN).
  Color of second leaf above the ear (at anthesis) (CR2LN) (Munsell value).
  Glume color bars perpendicular to their veins (glume bands) (GLCBN): can be described as (1) absent or (2) present.
  Anther color (Munsell value) (ANTCN).
  Pollen Shed (PLQUR): Can be described numerically, for example, 1-9 (0=male sterile).
  Number of leaves above the top ear node (LAERN).
  Number of lateral tassel branches that originate from the central spike (LTBRN).
  Number of ears per stalk (EARPN).
  Husk color (Munsell value) 25 days after 50% silk (fresh) (HSKCN).
  Husk color (Munsell value) 65 days after 50% silk: (dry) (HSKDN).
  Leaf marginal waves: Can be described numerically, for example, 1-9 (1=none) (MLWVR).
  Leaf longitudinal creases (LFLCR): Can be described numerically, for example, 1-9 (1=none).
  Length (cm) of ear leaf at the top ear node (ERLLN).
  Width (cm) of ear leaf at the top ear node at the widest point (ERLWN).
  Plant height (cm) to tassel tip (PLHTN).
  Plant height (cm) to the top ear node (ERHCN).
  Length (cm) of the internode between the ear node and the node above (LTEIN).
  Length (cm) of the tassel from top leaf collar to tassel tip (LTASN).
  Days from 50% silk to 25% grain moisture in adapted zone (DSGMN).
  Shank length (cm) (SHLNN).
  Ear length (cm) (ERLNN).
  Diameter (mm) of the ear at the midpoint (ERDIN).
  Weight (gm) of a husked ear (EWGTN).
  Kernel rows (KRRWR): Can be described as, for example, (1) Indistinct or (2) Distinct.
  Kernel row alignment (KRNAR): Can be described as, for example, (1) Straight; (2) Slightly Curved; or (3) Curved.
  Ear taper (ETAPR): Can be described as, for example, (1) Slight; (2) Average; or (3) Extreme.
  Number of kernel rows (KRRWN).
  Husk tightness 65 days after 50% silk (HSKTR): Can be described numerically, for example, 1-9 (1=loose).
  Diameter (mm) of the cob at the midpoint (COBDN).
  Yield (YKGHN) (kg/ha) Kg per Hectare.
  Hard endosperm color (KRCLN) (Munsell value)
  Aleurone color (ALECN) (Munsell value)
  Aleurone color pattern (ALCPR): Can be described, for example, as (1) homozygous or (2) segregating.
  Kernel length (mm) (KRLNN).
  Kernel width (mm) (KRWDN).
  Kernel thickness (mm) (KRDPN).
  One hundred kernel weight (gm) (K1KHN)
  Husk extension (HSKCR): Can be described as, for example, (1) Short (ear exposed); (2) Medium (8 cm); (3) Long (8-10 cm); or (4) Very long (>10 cm).
  Percent round kernels on 13/64 slotted screen (KRPRN).

Position of ear 65 days after 50% silk (HEPSR): Can be described as, for example, (1) Upright; (2) Horizontal; or (3) Pendent.

Percent dropped ears 65 days after anthesis (DPOPP).

Percent root lodging 65 days after anthesis (LRTRP).

Heat units to 25% grain moisture (from emergence) (HU25N).

Heat units from 50% silk to 25% grain moisture in adapted zone (HUSGN).

Other Definitions

A, AN, THE—As used herein, "a," "an" or "the" can mean one or more than one. For example, a cell can mean a single cell or a multiplicity of cells.

AND/OR—As used herein, "and/or" refers to and encompasses any and all possible combinations of one or more of the associated listed items, as well as the lack of combinations when interpreted in the alternative (or).

ABOUT—The term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

PLANT—The term "plant" is intended to encompass plants at any stage of maturity or development, including a plant that has been detasseled or from which seed or grain have been removed. A seed or embryo that will produce the plant is also included within the term plant.

PLANT PART—As used herein, the term "plant part" includes but is not limited to pollen, tassels, seeds, branches, fruit, kernels, ears, cobs, husks, stalks, root tips, anthers, stems, roots, flowers, ovules, stamens, leaves, embryos, meristematic regions, callus tissue, anther cultures, gametophytes, sporophytes, microspores, protoplasts, and the like. Tissue culture of various tissues of plants and regeneration of plants therefrom is well known in the art. Plant cell as used herein includes plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ. Thus, as used herein, a "plant cell" includes, but is not limited to, a protoplast, a gamete producing cell, and a cell that regenerates into a whole plant.

ALLELE—Any alternative forms of sequence. Diploid cells carry two alleles of the genetic sequence. These two sequence alleles correspond to the same locus (i.e., position) on homologous chromosomes.

ELITE INBRED, ELITE LINE—Maize plant that is substantially homozygous and which contributes useful agronomic and/or phenotypic qualities when used to produce hybrids that are commercially acceptable.

GENE SILENCING—The loss or inhibition of the expression of a gene.

GENOTYPE—genetic makeup.

LINKAGE—The tendency of a segment of DNA on the same chromosome to not separate during meiosis of homologous chromosomes. Thus during meiosis this segment of DNA remains unbroken more often than expected by chance.

LINKAGE DISEQUILIBRIUM—The tendency of alleles to remain in linked groups when segregating from parents to progeny more often than expected from chance.

LOCUS—A defined segment of DNA. This segment is often associated with an allele position on a chromosome.

PHENOTYPE—The detectable characteristics of a maize plant. These characteristics often are manifestations of the genotype/environment interaction.

BACKCROSS and BACKCROSSING refer to the process whereby a progeny plant is repeatedly crossed back to one of its parents. In a backcrossing scheme, the "donor" parent refers to the parental plant with the desired gene or locus to be Introduced. The "recipient" parent (used one or more times) or "recurrent" parent (used two or more times) refers to the parental plant into which the gene or locus is being Introduced. For example, see Ragot, M. et al. Marker-assisted Backcrossing: A Practical Example, in Techniques et Utilisations des Marqueurs Moleculaires Les Colloques, Vol. 72, pp. 45-56 (1995); and Openshaw et al., Marker-assisted Selection in Backcross Breeding, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

CROSS or CROSSED refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant) and use of haploid inducer to form haploid seeds. The term "crossing" refers to the act of using gametes via pollination to produce progeny.

CULTIVAR and VARIETY refer to a group of similar plants that by structural or genetic features and/or performance can be distinguished from other varieties within the same species.

TRANSGENE refers to any nucleotide sequence used in the transformation of a plant (e.g., maize), animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, is an organism into which a transgene has been delivered or introduced and the transgene can be expressed in the transgenic organism to produce a product, the presence of which can impart an effect and/or a phenotype in the organism.

INTRODUCE OR INTRODUCING (and grammatical equivalents thereof) in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part i.e. transformation. It also refers to both the natural and artificial transmission of a desired allele, transgene, or combination of desired alleles of a genetic locus or genetic loci, or combination of desired transgenes from one genetic background to another. For example, a desired allele or transgene at a specified locus can be transmitted to at least one progeny via a sexual cross between two parents of the same species, where at least one of the parents has the desired allele or transgene in its genome. Alternatively, for example, transmission of an allele or transgene can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele or transgene can be repeatedly backcrossed to a line having a desired genetic background and selected for the desired allele or transgene, with the result being that the desired allele or transgene becomes fixed in the desired genetic background.

I. Embodiments of the Invention

A. Inbred and Hybrid Production

Certain regions of the Corn Belt can have specific difficulties related to grain production that other regions may not have. Thus, the corn hybrids developed from inbreds should have traits that overcome or at least minimize these regional growing problems. Examples of these problems include Gray Leaf Spot infection in the eastern Corn Belt, cool temperatures during seedling emergence in the northern Corn Belt, Corn Lethal Necrosis (CLN) disease in the Nebraska region and soil with excessively high pH levels in the west. Hybrid combinations employ inbreds that address these specific issues resulting in the development of hybrids which are well adapted to niche production challenges. However, the aim of seed producers is to provide a number of traits to each inbred so that the corresponding hybrid combinations can be useful across broad regions of the Corn Belt. Biotechnology techniques offer tools, such as microsatellites, SNPs, RFLPs, RAPDs and the like, to breeders to accomplish the goal of providing desirable traits in inbreds.

To produce hybrids, inbreds are developed using numerous methods, which allow for the introduction of needed traits into the inbreds used in the hybrid combination. Hybrids are not often uniformly adapted for use throughout the entire U.S. Corn Belt, but most often are adapted for specific regions of the Corn Belts because for example, northern regions of the Corn Belt require shorter season hybrids than do southern regions. Hybrids that grow well in Colorado and Nebraska soils may not flourish in richer Illinois and Iowa soils. Thus, several different major agronomic traits are important in hybrid combination for growth in the various Corn Belt regions, and these traits have an impact on hybrid performance.

If there is a pool of desirable maize varieties for use as parents then development of a corn hybrid involves one step crossing the selected maize variety with at least one different maize variety to produce the hybrid progeny. This single crossing step is possible because breeders have been developing inbreds from different maize germplasm pools since the early 1900s, which can be used in hybrid combinations. However, to keep producing better and higher yielding hybrids, better inbreds must be developed. Inbred development involves the step of selecting plants from various germplasm pools, or from the same germplasm pool for making initial breeding crosses; and then either producing haploid seed from the cross and selfing as needed, or selfing the breeding crosses for several generations to produce a series of inbred lines, which, although different from each other, breed true and are highly uniform. During plant selection in each generation, uniformity of plant type is maintained to ensure homozygosity and phenotypic stability. A consequence of the homozygosity and homogeneity of the inbred lines is that the hybrid between a defined pair of inbreds, regardless of the method by which the inbreds were produced, will always be the same.

The maize variety and seed of the present invention can be employed to carry an agronomic package of this invention into a hybrid. Additionally, as described herein the inbred line can comprise one or more transgenes that are then introduced into the hybrid seed. When the maize variety parents that give a superior hybrid have been identified, the hybrid seed can be reproduced indefinitely as long as the homogeneity of the maize variety parents is maintained.

Any breeding methods using the maize variety NPJC6794, and its progeny are part of this invention. Inbred development can be accomplished by different methods, for example, pedigree selection, backcrossing, recurrent selection, haploid/doubled haploid production. The haploid/doubled haploid process of developing developing inbreds starts with the induction of a haploid by using, for example, KWS inducers lines, Krasnador inducers lines, stock six inducer lines or the like, or by selecting the gamete cell in an anther culturing protocol. The haploid cell is then doubled, and the doubled haploid plant is produced. Sometimes this doubled haploid can be used as an inbred but sometimes it is further self pollinated to finish the inbred development. Another breeding process is pedigree selection which uses the selection in an F2 population produced from a cross of two genotypes (often elite inbred lines), or selection of progeny of synthetic varieties, open pollinated, composite, or backcrossed populations. Pedigree selection is effective for highly heritable traits but other traits, such as yield, require replicated test crosses at a variety of stages for accurate selection.

The maize variety and hybrid corn lines of the present invention can be employed in a variety of breeding methods that can be selected, depending on the mode of reproduction, the trait and/or the condition of the germplasm. Thus, any breeding methods using the inbred corn line NPJC6794 or it progeny are part of this invention. Such methods can include, but are not limited to, marker assisted breeding, selection, selfing, backcrossing, hybrid production, and crosses to populations.

All plants and plant cells produced using maize variety NPJC6794 are encompassed within the present invention, which also encompasses the corn variety used in crosses with other, different, corn varieties to produce corn hybrid seeds and hybrid plants and the grain produced on the hybrid plant. This invention includes progeny plants and plant cells, which upon growth and differentiation produce corn plants having the physiological and morphological characteristics of the maize variety NPJC6794 when grown in the same environmental conditions.

Maize breeders select for a variety of traits in inbred plants that impact hybrid performance in addition to selecting for acceptable parental traits. Such traits include, but are not limited, to yield potential in hybrid combination, dry down, maturity, grain moisture at harvest, green snap, resistance to root lodging, resistance to stalk lodging, grain quality, disease and insect resistance, ear, and plant height. Additionally, because hybrid performance may differ in different soil types such as those having low levels of organic matter, clay, sand, black, high pH, or low pH; or in different environments such as wet environments, drought environments, and no tillage conditions multiple trials testing for agronomic traits must be run to assert hybrid performance across environments. These traits are governed by a complex genetic system that makes selection and breeding of an inbred line extremely difficult. However, even if an inbred, in hybrid combination, has excellent yield (a desired characteristic), it may not be useful for hybrid seed production if the inbred lacks acceptable parental traits, for example, seed size, pollen production, good silks, plant height, etc.

The following example is provided to illustrate the difficulty of breeding and developing inbred lines. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are not single dominant genes; they are multi-genetic with additive gene action but not dominant gene action. Thus, the general approach of producing a non-segregating F1 generation and self pollinating to produce an F2 generation that segregates for traits and then selecting progeny from the F2 generation with the desired visual traits does not easily lead to a useful inbred. Great care and breeder expertise must be used in the selection of breeding material to continue to increase yield and enhance desirable agronomic features of inbreds and resultant commercial hybrids.

In one embodiment, a method of producing a plant of this invention is by planting the seed of NPJC6794, which is substantially homozygous, self-pollinating or sib pollinating the resultant plant in isolate environment, and harvesting the resultant seed. The F1 hybrid seed can be produced using two distinct inbreds, the male inbred contributing pollen to the female seed producing parent, the female seed producing parent, on the other hand, is not contributing pollen to the seed. Thus, in some embodiments, a method is provided for producing an hybrid maize seed by crossing a plant of maize variety NPJC6794 with a different maize plant (e.g., a different inbred line), and harvesting the resultant hybrid maize seed. A maize plant of the present invention can act as a male or female part in hybrid production.

A method is also provided for producing maize seed comprising growing the plant of this invention until seed is produced and harvesting the seed, wherein the harvested seed is inbred or hybrid or haploid seed. Plants and plant parts produced by the seed of this method is also provided herein. Additionally, provided herein is a method of producing hybrid seed corn from this inbred corn line and producing hybrid plants and seeds from the hybrid seed corn of this invention.

Thus, in some embodiments, the invention provides hybrid seed, produced by planting, in pollinating proximity, seeds of corn inbred line NPJC6794 and seeds of another inbred line. The corn plants resulting from said planting are cultivated; emasculation of one of the inbred lines (i.e., the selected inbred plant) and allowing pollination to occur. Seeds produced by plants of the selected inbred can be harvested. In further embodiments, seeds of corn inbred line NPJC6794 are planted and cultivated. Alternatively, emasculated plants are pollinated with preserved maize pollen (as described in U.S. Pat. No. 5,596,838 to Greaves). The seeds produced by the inbred line NPJC6794 pollinated with the preserved pollen can be harvested. The hybrid seed produced by the hybrid combination of plants of inbred corn seed designated NPJC6794 and plants of another inbred line or produced by the plants of inbred corn seed designated NPJC6794 pollinated by preserved pollen are included in the present invention. This invention further encompasses hybrid plants and plant parts thereof including but not limited to the grain and pollen of the plant grown from this hybrid seed.

In two alternative embodiments, the method is provided for producing an hybrid maize seed, the method comprising crossing a plant of maize variety plant NPJC6794 with a different maize variety (e.g., a different inbred line), wherein the pollen of the maize variety NPJC6794 pollinates the different maize variety, or in the alternative the pollen of the different maize variety pollinates maize variety NPJC6794, and the resultant hybrid maize seed is harvested.

In particular embodiments, this invention is directed to the unique combination of traits that combine in corn line NPJC6794. Also encompassed within this invention is an F1 hybrid maize seed comprising an inbred maize plant cell of inbred maize plant NPJC6794.

The invention further relates to methods for producing other maize breeding lines derived from the corn inbred of this invention by crossing the maize inbred plant NPJC6794 with a second maize plant and growing the progeny seed to yield a inbred NPJC6794-derived maize plant. Thus, in some embodiments of this invention, a method is provided for producing a maize plant derived from the inbred plant NPJC6794, the method comprising the steps of: (a) growing a hybrid progeny plant wherein the maize variety of this invention is a parent (b) crossing the hybrid progeny plant with itself or a different plant to produce a seed of a progeny plant; (c) growing the progeny plant from said seed and crossing the progeny plant with itself or a different plant; and (d) repeating steps (c) for an additional generation to produce a maize plant derived from the inbred plant NPJC6794. The present invention also provides a maize seed produced by crossing the plant of this invention with itself or a different maize plant.

Thus, other aspects of this invention include a method for developing a maize plant in a maize plant breeding program, comprising applying plant breeding techniques comprising recurrent selection, backcrossing, pedigree breeding, marker enhanced selection, haploid/double haploid production, or transformation to the maize plant of this invention, or its parts, wherein application of said techniques results in development of a maize plant.

B. Transfer of Traits into Inbred Corn Line NPJC6794

The use of an inbred maize plant, such as the inbred of the present invention, as a recurrent parent in a breeding program is referred to as backcrossing. Backcrossing is often employed to introduce a desired trait (e.g., targeted trait or trait of interest) or trait(s), either transgenic or nontransgenic, into a recurrent parent. A plant with the desired trait or locus is crossed into a recurrent maize parent usually in one or more backcrosses. If markers are employed to assist in selection of progeny that have the desired trait and recurrent parent background genetics, then the number of backcrosses needed to recover the recurrent parent with the desired trait or locus can be relatively few, e.g., two or three. However, 3, 4, 5 or more backcrosses are often required to produce the desired inbred with the gene or locus conversion in place. The number of backcrosses needed for a trait introduction is often linked to the genetics of the line carrying the trait and the recurrent parent and the genetics of the trait. Multigenic traits, recessive alleles and unlinked traits can affect the number of backcrosses that may be necessary to achieve the desired backcross conversion of the inbred.

Basic maize crossing techniques, as well as other corn breeding methods including recurrent, bulk or mass selection, pedigree breeding, open pollination breeding, marker assisted selection/breeding, double haploids development and selection breeding are well known in the art (see, e.g., Hallauer, *Corn and Corn Improvement*, Sprague and Dudley, 3rd Ed. 1998). Dominant, single gene traits or traits with obvious phenotypic changes are particularly well managed in backcrossing programs, as are well known in the art. A backcross conversion or locus conversion both refer to a product of a backcrossing program.

A backcrossing program is more complicated when the trait is a recessive gene. A determination of the presence of the recessive gene requires the use of some testing to determine if the trait has been transferred. Use of markers to detect the gene reduces the complexity of trait identification in the progeny. A marker specific for a recessive trait, such as a single nucleotide polymorphism (SNP), can increase the efficiency and speed of tracking the recessive trait within a backcrossing program.

The last backcross generation can be selfed, if necessary, to give pure breeding progeny for the nucleic acid(s) being transferred. The resulting plants generally have essentially all of the morphological and physiological characteristics of the inbred corn line of interest, in addition to the transferred trait(s) (e.g., one or more gene traits). The exact backcrossing protocol will depend on the trait being altered to determine an appropriate testing protocol.

Thus, in some embodiments, one or more traits can be introduced into a plant of this invention using any method known in the art for introducing traits into plants. Nucleotide sequences encoding traits of interest can all be located at the same genomic locus in the donor, non-recurrent parent, and in the case of transgenes, can be part of a single DNA construct integrated into the donor's genome or into additional chromosomes integrated into the donor's genome. Alternatively, if the nucleotide sequences of interest are located at different genomic loci in the donor, non-recurrent parent, backcrossing can be carried out to establish all of the morphological and physiological characteristics of the plant of the invention in addition to the nucleotide sequences encoding the traits of interest in the resulting maize inbred line.

Accordingly, the present invention provides a method of introducing or introgressing at least one desired trait into the maize inbred line NPJC6794, comprising the steps of: (a) crossing a plant grown from the seed of the maize inbred line NPJC6794 (which is the recurrent parent, representative seed of which has been deposited), with a donor plant of another maize line that comprises at least one desired trait to produce F1 plants; (b) selecting F1 plants having the at least one desired trait to produce the selected F1 progeny plants; (c) crossing the F1 plants of (b) with the recurrent parent to produce backcrossed progeny plants having the at least one desired trait; (d) selecting for backcrossed progeny plants that have at least one of the desired traits and physiological and morphological characteristics of maize inbred line of the recurrent parent to produce selected backcrossed progeny plants; and (e) repeating the crossing of the selected backcrossed progeny to the recurrent parent of step (c) and the selecting of step (d) in succession to produce a plant that comprises at least one desired trait and all of the physiological and morphological characteristics of the maize inbred line NPJC6794 when grown in the same environmental conditions (e.g., essentially the recurrent parent having the at least one desired trait).

In some embodiments of this invention, the at least one desired trait comprises the trait of male sterility, herbicide resistance, insect resistance, disease resistance, altered starch, modified amylase starch, amylose starch, waxy starch, or any combination thereof. In other embodiments of this invention, the at least one desired trait is conferred by a nucleic acid molecule encoding an enzyme that includes, but is not limited to, a phytase, a stearyl-ACP desaturase, a fructosyltransferase, a levansucrase, an amylase, an invertase, a starch branching enzyme, or any combination thereof.

In some embodiments, the selecting and crossing steps of (e) are repeated at least 3 times in order to produce a plant that comprises the at least one desired trait and all of the physiological and morphological characteristics of the maize inbred line of the recurrent parent in the present invention (listed in Table 1) when grown under the same environmental conditions (as determined at the 5% significance level). In other embodiments, the selecting and crossing steps of (e) are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to produce a plant that comprises the at least one desired trait and all of the physiological and morphological characteristics of the maize inbred line of the recurrent parent in the present invention. In other embodiments, the crossing and growing steps of (a) and (b) in step (c) are repeated from 0 to n times (wherein n can be any number) in order to produce a plant that comprises the at least one desired trait and all of the physiological and morphological characteristics of the maize inbred line of the recurrent parent in the present invention.

The method of introducing traits as described herein can be done with fewer back crossing events if the trait and/or the genotype of the present invention is selected for or identified through the use of markers. SSR, microsatellites, single nucleotide polymorphisms (SNPs) and the like decrease the amount of breeding time required to locate a line with the desired trait or traits and the characteristics of the present invention. Backcrossing in two or even three traits (for example the glyphosate resistance, Europe corn borer resistance, corn rootworm resistance) is routinely done with the use of marker assisted breeding techniques and or selection pressure testing. Introduction of transgenes or mutations into a maize line is known as single gene conversion. More than one gene and, in particular, transgenes and/or mutations that are readily tracked with markers, can be moved during the same "single gene conversion" process. This single gene conversion process results in a line comprising more desired or targeted traits than just the one but still having the characteristics of the plant line of the present invention plus those characteristics added by the desired/targeted traits.

Genetic variants of inbred corn line NPJC6794 that are naturally-occurring or created through traditional breeding methods using inbred corn line NPJC6794 are also intended to be within the scope of this invention. In particular embodiments, the invention encompasses plants of this invention and parts thereof further comprising one or more additional traits, in particular, specific, single gene transferred traits. Examples of traits that may be transferred include, but are not limited to, herbicide resistance, disease resistance (e.g., bacterial, fungal or viral disease), nematode resistance, tolerance to abiotic stresses (e.g., drought, temperature, salinity), yield enhancement, improved nutritional quality (e.g., oil starch and protein content or quality), modified metabolism (e.g. protein, carbohydrates, starch, amylase) altered reproductive capability (e.g., male sterility) or other agronomically important traits.

Such traits may be introduced into a plant of this invention from another corn line or through direct transformed into a plant of this invention (discussed below). One or more new traits can be transferred to a plant of this invention, or, alternatively, one or more traits of a plant of this invention are altered or substituted. The introduction of the trait(s) into a plant of this invention may be achieved by any method of plant breeding known in the art, for example, pedigree breeding, backcrossing, doubled-haploid breeding, and the like.

C. Nucleic Acids for Introduction into Maize Plants of the Present Invention

As would be appreciated by one of skill in the art, any nucleotide sequence of interest can be introduced into the plants and/or parts thereof of the present invention. Some exemplary nucleotide sequences and traits that may be used with the present invention are provided herein.

Methods and techniques for introducing and/or introgressing a trait or nucleotide sequence into a plant of the present invention through breeding, transformation, site specific insertion, mutation and the like, are well known and understood by those of ordinary skill in the art. Nonlimiting examples of such techniques include, but are not limited to, anther culturing, haploid/double haploid production, (including, but not limited to, stock six, which is a breeding/selection method using color markers), transformation, irradiation to produce mutations, and chemical or biological mutation agents.

1. Male Sterility

As described herein, the inbred and hybrid lines plants of this invention can comprise male sterility. Male sterility and/or CMS (cytoplasmic male sterility) systems for maize parallel the CMS type systems, were first used in maize in the seventies but were to widely embraced; however, CMS has have been routinely used in hybrid production in sunflower plants. A number of methods are available to generate male sterile plants including, but not limited to, introduction into the plant of nucleotide sequences that confer male sterility, by chemicals, and/or by a mixture of nucleotide sequences conferring male sterility, natural or induced sterility mutations, and/or chemicals.

As described herein, the inbred and hybrid plants of this invention can comprise the trait of male sterility. Male sterility is useful, for example, in hybrid production for elimination of pollen shed from the seed producing parent. Sterility can be produced by pulling or cutting tassels from the plant, i.e., detasseling, use of gametocides, or use of genetic material to render the plant sterile using a CMS type of genetic control or a nuclear genetic sterility, use of chemicals, for example herbicides that inhibit or kill pollen. The seed producing parent can be grown in isolation from other pollen sources except for the pollen source which is the male fertile inbred, which serves as the male parent in the hybrid. To facilitate pollination of the seed producing (female) parent, the male fertile inbreds can be planted in rows near the male sterile (female) inbred.

In hybrid seed production using the standard CMS system, three different maize lines are employed. The first line is cytoplasmic male-sterile. This line will be the seed producing parent line. The second line is a fertile inbred that is the same as or isogenic with the seed producing inbred parent but lacking the trait of male sterility. This is a maintainer line used to make new inbred seed of the seed producing male sterile parent. The third line is a different inbred which is fertile, has normal cytoplasm and carries a fertility restoring gene. This line is called the restorer line in the CMS system. The CMS cytoplasm is inherited from the maternal parent (or the seed producing plant); therefore in order for the hybrid seed produced on such a plant to be fertile, the pollen used to fertilize this plant must carry the restorer gene. The positive aspect of this process is that it allows hybrid seed to be produced without the need for detasseling the seed parent. However, this system does require breeding of all three types of lines: 1) a male sterile line-to carry the CMS, 2) a maintainer line; and 3) a line carrying the fertility restorer gene.

Accordingly, in some embodiments of the present invention, sterile hybrids are produced and the pollen necessary for the formation of grain on these hybrids is supplied by interplanting of fertile inbreds in the field with the sterile hybrids.

A number of additional techniques exist that are designed to avoid detasseling in maize hybrid production. Nonlimiting examples of such techniques include switchable male sterility, lethal genes in the pollen or anther, inducible male sterility and/or male sterility genes with chemical restorers. Additional examples include, but are not limited to, U.S. Pat. No. 6,025,546, which describes the use of tapetum-specific promoters and the barnase gene to produce male sterility, and U.S. Pat. No. 6,627,799, which describes modifying stamen cells to provide male sterility. Therefore, one aspect of the present invention provides a corn plant of this invention comprising one or more nucleotide sequences that restore male fertility to male-sterile maize inbreds or hybrids and/or one or more nucleotide sequences or traits to produce male sterility in maize inbreds or hybrids.

Furthermore, methods for genetic male sterility are disclosed in EPO Publication No. 89/3010153.8, PCT Publication No. WO 90/08828 and U.S. Pat. Nos. 4,654,465, 4,727, 219, 3,861,709, 5,432,068 and 3,710,511. Gametocides, some of which are taught in U.S. Pat. No. 4,735,649 (incorporated by reference) can be employed to make the plant male sterile. Gametocides, including, but not limited to, glyphosate, and its derivatives are chemicals or substances that negatively affect the pollen or at least the fertility of the pollen and provide male sterility to the seed producing parent.

It is noted that hybrid production employing any most forms of male sterility including mechanical emasculation can have a small occurrence of self pollinated female inbred seeds along with the intended F1 hybrid seeds. Great measures are taken to avoid the inbred seed production in a hybrid seed production field; but inbred seed can occur during F1 seed production and it gets harvested with the hybrid seed harvest.

Inbred seed in a sample of hybrid seed may be detected using molecular markers. Alternatively, the seed sample can be planted and an inbred capture process can be used to isolate inbred seed from the hybrid F1 seed sources. The inbred plants tend to be readily distinguished from the hybrid plants due to the inbreds having a stunted appearance, i.e., shorter plant, smaller ear, etc. Self pollination of the stunted plants grown from these identified putative inbred plants produces either the female inbred seed, if it was an inbred plant or if it was a weak hybrid than the hybrid kernel will be F2 seed. The resultant plants are observed for size or they can be tested by markers to identify any inbred plants. The identified inbred plants can be selected and self-pollinated to form the inbred seed.

2. Additional Traits of Interest

As discussed above, backcrossing of recessive traits has allowed known mutant traits to be moved into elite germplasm. Mutations can be introduced in germplasm by the plant breeder. Mutations can also result from plant or seed or pollen exposure to temperature alterations, culturing, radiation in various forms, chemical mutagens like EMS and like, as are well known in the art. Non-limiting examples of mutant genes that have been identified and introduced into elite maize useful with this invention include the genotypes numerous sterility and partial sterility genes, herbicide resistant mutants, phytic acid mutants, waxy (wx), amylose extender (ae), dull (du), horny (h), shrunken (sh), brittle (bt), floury (fl), opaque (o), and sugary (su). Some of the bracketed nomenclature for these mutant genes is based on the effect these mutant genes have on the physical appearance and phenotype of the kernel.

Additional mutations useful with this invention include, but are not limited to, those that result in the production of starch with markedly different functional properties even though the phenotypes of the seed and plant remain the same. Such genotypes include, but are not limited to, sugary-1 (su1), sugary-2 (su2); shrunken 1 (sh1) and shrunken 2 (sh2).

Additional, exemplary nucleic acid molecules that can be introduced into a plant of the present invention include, but are not limited to, nucleotide sequences that confer insect resistance including, but not limited to, resistance to Corn Rootworm in the event DAS-59122-7, Mir604 Modified Cry3A event, Event 5307 Syngenta, MON 89034, MON 88017 *Bacillus thuringiensis* (Cry genes) Cry34/35Ab1, Cry1A.105, Cry1F, Cry2Ab2, Cry1A, Cry1AB, Cry1Ac Cry3Bb1, or any combination thereof. Thus, for example, in some embodiments, an insecticidal gene that can be introduced into a plant of the present invention is a Cry1Ab gene or a portion thereof, for example, introduced into a plant of the present invention from a maize line comprising a Bt-11 event as described in U.S. Pat. No. 6,114,608, (incorporated herein by reference) or from a maize line comprising a 176 Bt event as described in Koziel et al. (Biotechnology 11: 194-200 (1993)).

In other embodiments of this invention, nucleotide sequences that confer disease resistance are introduced and/or transformed into the inbred line. Non-limiting examples of such nucleotide sequences include, but are not limited to, a nucleotide sequence encoding Mosaic virus resistance, a nucleotide sequence encoding an MDMV strain B coat protein whose expression confers resistance to mixed infections of maize dwarf mosaic virus and maize chlorotic mottle virus (Murry et al. *Biotechnology* (1993) 11:1559-64, a nucleotide sequence conferring resistance to Northern corn leaf blight, and a nucleotide sequence conferring resistance to Southern corn leaf blight, or any combination thereof.

In additional embodiments, nucleotide sequences that confer herbicide resistance/tolerance are useful with the present invention, non-limiting examples of which comprise nucleotide sequences conferring resistance to herbicides for example imazethapyr, glyphosate, dicamba, and the like, and nucleotide sequences encoding Pat (phosphinothricin-N-acetyltransferase), Bar (bialophos), altered acetohydroxyacid synthase (AHAS) (confers tolerance to various imidazolinone or sulfonamide herbicides) (U.S. Pat. No. 4,761,373), or any combination thereof.

Additional, non-limiting examples of nucleotide sequences conferring herbicide resistance/tolerance that are useful with the present invention, include nucleotide sequences conferring tolerance to imidazolinones (e.g., a "IT" or "IR" trait). U.S. Pat. No. 4,975,374 (incorporated herein by reference), relates to plant cells and plants containing a gene encoding a mutant glutamine synthetase (GS) having resistance to inhibition by herbicides that are known to inhibit GS, e.g., phosphinothricin and methionine sulfoximine. Also, expression of a *Streptomyces* bar gene encoding a phosphinothricin acetyl transferase in maize plants confers tolerance to the herbicide phosphinothricin or glufosinate (U.S. Pat. No. 5,489,520). U.S. Pat. No. 5,013,659, (incorporated herein by reference), is directed to plants that express a mutant acetolactate synthase (ALS) that renders the plants resistant to inhibition by sulfonylurea herbicides. U.S. Pat. No. 5,162,602 discloses nucleotide sequences that confer resistance to cyclohexanedione and aryloxyphenoxypropanoic acid herbicides. The tolerance is conferred by an altered acetyl coenzyme A carboxylase (ACCase). U.S. Pat. No. 5,554,798 discloses transgenic glyphosate tolerant maize plants, which tolerance is conferred by an altered 5-enolpyruvyl-3-phosphoshikimate (EPSP) synthase gene. U.S. Pat. No. 5,804,425 discloses transgenic glyphosate tolerant maize plants, which tolerance is conferred by an EPSP synthase gene derived from *Agrobacterium tumefaciens* CP-4 strain. Also, tolerance to a protoporphyrinogen oxidase inhibitor is achieved by expression of a protoporphyrinogen oxidase enzyme in plants as disclosed in U.S. Pat. Nos. 5,767,373, 6,282,837, or WO 01/12825. Another trait transferable to the plant of the present invention confers a safety effect or additional tolerance to an inhibitor of the enzyme hydroxyphenylpyruvate dioxygenase (HPPD) and transgenes conferring such trait are, for example, described in PCT Publication Nos. WO 9638567, WO 9802562, WO 9923886, WO 9925842, WO 9749816, WO 9804685 and WO 9904021. Any of the above described nucleotide sequences identified to confer herbicide resistance/tolerance can be used to confer such resistance/tolerance to the plants of the present invention. These nucleotide sequences can be introduced or transformed into the plants of the present invention alone or in any thereof.

Additional embodiments of this present invention include nucleotide sequences conferring altered traits. Such altered traits include, but are not limited to, lignin composition and production (including but not limited to nucleotide sequences conferring the brown mid-rib trait), flowering, senescence, and the like, or any combination thereof.

The present invention also encompasses methods for the introduction into a plant of this invention, one or more traits that have an effect on products or by-products of the corn plant such as the sugars, oils, protein, ethanol, biomass and the like. Such traits can include those that result in the formation of an altered carbohydrate or altered starch. An altered carbohydrate or altered starch can be formed as a result of expression of one or more introduced nucleotide sequences that affect synthases, branching enzymes, pullanases, debranching enzymes, isoamylases, alpha amylases, beta amylases, AGP, ADP and other enzymes which affect amylose and/or amylopectin ratio or content, or the branching pattern of starch.

Introduced fatty acid modifying nucleotide sequences can also affect starch content and therefore can be employed in the methods and plants of this invention. Additionally, introduced nucleotide sequences that are associated with or affect starch and carbohydrates can be adapted so that the nucleotide sequence or its enzyme product does not necessarily alter the form or formation of the starch or carbohydrate of the seed or plant but instead the introduced nucleotide sequence or its RNA, polypeptide, protein or enzyme can be adapted to degrade, alter, or otherwise change the formed starch or carbohydrate. Examples of this technology are shown, for example, in U.S. Pat. Nos. 7,033,627, 5,714,474, 5,543,570, 5,705,375, 7,102,057, each of which are incorporated by reference. An example of the use of an alpha amylase adapted in this manner in maize is described in U.S. Pat. No. 7,407,677, the content of which is also incorporated herein by reference.

By way of example only, specific events (followed by their APHIS petition numbers) that can be Introduced into maize plants by backcross breeding techniques include the glyphosate tolerant event GA21 (97-09901p), the glyphosate tolerant event NK603 (00-011-01p), the glyphosate tolerant/Lepidopteran insect resistant event MON 802 (96-31701p) Mon810, the Lepidopteran insect resistant event DBT418 (96-29101p), the male sterile event MS3 (95-22801p), the Lepidopteran insect resistant event Bt11 (95-19501p), the phosphinothricin tolerant event B16 (95-14501p), the Lepidopteran insect resistant events MON 80100 (95-09301p) and MON 863 (01-137-01p), the phosphinothricin tolerant events T14, T25 (94-35701p), the Lepidopteran insect resistant event 176 (94-31901p), Western corn rootworm (04-362-01p), the phosphinothricin tolerant and Lepidopteran insect resistant event CBH-351 (92-265-01p), the transgenic corn event designated 3272 as described in US Patent Publication No. 20060230473 (hereby incorporated by reference) and the like, or any combination thereof.

In some embodiments, a combination of traits can be transformed or introduced into the plants of the present invention. This in some embodiments, a transgene can be introduced into a plant of a present invention which comprises a nucleotide sequence conferring tolerance to a herbicide and at least another nucleotide sequence encoding another trait, such as for example, an insecticidal protein. Such a combination of single traits can be, for example, a Cry1Ab gene and a bar gene. The introduction of a Bt11 event into a maize line, such as the line of the present invention, by backcrossing is exemplified in U.S. Pat. No. 6,114,608, and the present invention includes methods of introducing a Bt11 event into a plant of the present invention and to progeny thereof using, e.g., markers as described in U.S. Pat. No. 6,114,608.

D. Transformation of Corn Inbred NPJC6794 Plants and/or Parts Thereof

The term transgenic plant refers to a plant having one or more genetic sequences that are introduced into the genome of a plant by a transformation method and the progeny thereof. With the advent of molecular biological techniques that have allowed the isolation and characterization of nucleic acids that encode specific protein products, scientists in the field of plant biology developed a strong interest in engineering the genome of plants to contain and express foreign nucleic acids, or additional, or modified versions of native or endogenous nucleic acids (perhaps driven by different promoters) in order to alter the traits of a plant in a specific manner. Such foreign, additional and/or modified nucleic acids are referred to herein collectively as "transgenes." The term "transgene," as used herein, is not necessarily intended to indicate that the foreign nucleic acid is from a different plant species. For example, the transgene may be a particular allele derived from another corn line or may be an additional copy of an endogenous gene. Over the last twenty to twenty-five years several methods for producing transgenic plants have been developed. Therefore, in particular embodiments, the present invention also encompasses transformed plants and/or parts thereof (e.g., cells, seeds, anthers, ovules, and the like) of inbred corn line NPJC6794.

Transformation methods are techniques for integrating new nucleotide sequence(s) into the genome of a plant by recombinant nucleic acid technology, rather than by standard breeding practices. However, once a transgene is introduced into plant material and stably integrated, standard breeding practices can be used to move the transgene into other germplasm.

Plant transformation generally involves the construction of an expression vector that will function in plant cells. Such a vector comprises DNA or RNA comprising a nucleic acid under control of, or operatively linked to, a regulatory element (for example, a promoter). The expression vector may contain one or more such operably linked nucleic acid/regulatory element combinations. The vector(s) may be in the form of, for example, a plasmid or a virus, and can be used, alone or in combination with other vectors, to provide transformed maize plants, using transformation methods as described below to incorporate transgenes into the genetic material of the maize plant(s).

Any transgene(s) known in the art may be introduced into a maize plant, tissue, cell or protoplast according to the present invention, e.g., to improve commercial or agronomic traits, herbicide resistance, disease resistance (e.g., to a bacterial fungal or viral disease), insect resistance, nematode resistance, yield enhancement, nutritional quality (e.g., oil starch and protein content or quality), altered reproductive capability (e.g., male sterility), and the like or any combination thereof. Alternatively, a transgene may be introduced for the production of recombinant proteins (e.g., enzymes) or metabolites.

A recombinant nucleic acid molecule of the invention can be introduced into a plant cell in a number of art-recognized ways. Suitable methods of transforming plant cells include microinjection (Crossway et al. *BioTechniques* 4:320-334 (1986)), electroporation (Riggs et al. *Proc. Natl. Acad. Sci. USA* 83:5602-5606 (1986)), *Agrobacterium*-mediated transformation (Hinchee et al. *Biotechnology* 6:915-921 (1988)), direct gene transfer (Paszkowski et al. *EMBO J.* 3:2717-2722 (1984)), ballistic particle acceleration using devices available, e.g., from Agracetus, Inc., Madison, Wis. and Dupont, Inc., Wilmington, Del. (see, for example, Sanford et al., U.S. Pat. No. 4,945,050; and McCabe et al. *Biotechnology* 6:923-926 (1988)), protoplast transformation/regeneration methods (see U.S. Pat. No. 5,350,689, issued Sep. 27, 1994 to Ciba-Geigy Corp.), Whiskers technology (See U.S. Pat. Nos. 5,464,765 and 5,302,523) and pollen transformation (see U.S. Pat. No. 5,629,183). See also Weissinger et al. *Annual Rev. Genet.* 22:421-477 (1988); Sanford et al. *Particulate Science and Technology* 5:27-37 (1987) (onion); Christou et al. *Plant Physiol.* 87:671-674 (1988) (soybean); McCabe et al. *Bio/Technology* 6:923-926 (1988) (soybean); Datta et al. *Bio/Technology* 8:736-740 (1990) (rice); Klein et al. *Proc. Natl. Acad. Sci. USA* 85:4305-4309 (1988) (maize); Klein et al. *Bio/Technology* 6:559-563 (1988) (maize); Klein et al. *Plant Physiol.* 91:440-444 (1988) (maize); Fromm et al., *Bio/Technology* 8:833-839 (1990); Gordon-Kamm et al. *Plant Cell* 2:603-618 (1990) (maize); and U.S. Pat. Nos. 5,591,616 and 5,679,558 (rice).

A vector or nucleic acid construct of this invention can comprise leader sequences, transit polypeptides, promoters, terminators, genes or nucleotide sequences of interest, introns, nucleotide sequences encoding genetic markers, etc., and any combination thereof. The nucleotide sequence(s) of the vector or nucleic acid construct can be in sense, antisense, partial antisense, or partial sense orientation in any combination and multiple gene or nucleotide sequence copies can be used. The transgene or nucleotide sequence can come from a plant as well as from a non-plant source (e.g., bacteria, yeast, animals, and viruses)

A vector or nucleic acid construct comprising a transgene that is to be Introduced into a plant of this invention can comprise the transgene and/or encoding nucleotide sequence under the control of a promoter appropriate for the expression of the transgene and/or nucleotide sequence at the desired time and/or in the desired tissue or part of the plant. Constitutive or inducible promoters can be used, as are well known in the art. The vector or nucleic acid construct carrying the transgene and/or encoding nucleotide sequence can also comprise other regulatory elements such as, e.g., translation enhancers or termination signals. In some embodiments, the transgene or encoding nucleotide sequence is transcribed and translated into a protein. In other embodiments, the vector or nucleic acid construct can comprise a nucleotide sequence that encodes an antisense RNA, a sense RNA that is not translated or only partially translated, a tRNA, a rRNA and/or a snRNA, as are well known in the art.

E. Plant Tissue Culture and Regeneration

Plant cells, which have been transformed by any method known in the art, can also be regenerated to produce intact plants using known techniques. Plant regeneration from cultured protoplasts is described in Evans et al., Handbook of Plant Cell Cultures, Vol. 1: (MacMilan Publishing Co. New York, 1983); and Vasil I. R. (ed.), Cell Culture and Somatic Cell Genetics of Plants, Acad. Press, Orlando, Vol. 1, 1984, and Vol. II, 1986). It is known that practically all plants can be regenerated from cultured cells or tissues.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. A large number of plants have been shown capable of regeneration from transformed individual cells to obtain transgenic whole plants. Patents and patent publications cited as exemplary for the processes for transforming plant cells and regenerating plants are the following: U.S. Pat. Nos. 4,459,355, 4,536,475, 5,464,763, 5,177,010, 5,187,073, 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253 and 5,405,765; European Patent Nos. EP 267,159, EP 604 662, EP 672 752, EP 442 174, EP 486 233, EP 486 234, EP 539 563 and EP 674 725, and PCT Publication Nos. WO 91/02071 and WO 95/06128.

The use of pollen, cotyledons, zygotic embryos, meristems and ovum as the target tissue for transformation can eliminate or minimize the need for extensive tissue culture work. Generally, cells derived from meristematic tissue are useful. The method of transformation of meristematic cells of cereal is taught in PCT Publication No. WO96/04392. Any number of various cell lines, tissues, calli and plant parts can and have been transformed by those having knowledge in the art. Methods of preparing callus or protoplasts from various plants are well known in the art. Cultures can be initiated from most of the above-identified tissues. The only requirement of the plant material to be transformed is that it can ultimately be used to produce a transformed plant.

In Duncan et al. (*Planta* 165:322-332 (1985)) studies were conducted that demonstrated that 97% of plants cultured that produced callus were capable of plant regeneration. Subsequent experiments with both inbreds and hybrids showed that 91°/o appeared capable of producing regenerable callus. In a further study (Songstad et al. *Plant Cell Reports* 7:262-265 (1988)), several media additions were identified that enhanced regenerability of callus of two inbred lines. Other published reports indicated that "nontraditional" tissues are capable of producing somatic embryogenesis and plant regeneration. Rao et al. (*Maize Genetics Cooperation Newsletter* 60:64-65 (1986)) describes somatic embryogenesis from glume callus cultures and Conger et al. (*Plant Cell Reports* 6:345-347 (1987)) describes somatic embryogenesis from the tissue cultures of maize leaf segments. Thus, it is clear from the literature that the state of the art is such that these methods of obtaining plants from callus are, and were, "conventional" in the sense that they are routinely used and have a very high rate of success.

Tissue culture procedures of maize are described in Green and Rhodes ("Plant Regeneration in Tissue Culture of Maize" in *Maize for Biological Research* (Plant Molecular Biology Association, Charlottesville, Va. at 367 372 (1987)) and in Duncan, et al. ("The Production of Callus Capable of Plant Regeneration from Immature Embryos of Numerous *Zea mays* Genotypes" *Planta* 165: 322-332 (1985)). Thus, another aspect of this invention is to provide cells that upon growth and differentiation produce maize plants having the physiological and morphological characteristics of the plants of the present invention.

Accordingly, in some embodiments, the present invention provides a tissue culture of regenerable cells of NPJC6794, wherein the cells of the tissue culture regenerate plants that express the genotype of NPJC6794. The tissue culture can be but is not limited to tissue culture derived from leaf, pollen, embryo, root, root tip, guard cell, ovule, seed, anther, silk, flower, kernel, ear, cob, husk and stalk, cell and protoplast thereof. In some aspects of this invention, additionally provided is a tissue culture of regenerable cells of hybrid plants produced from NPJC6794 germplasm. A corn plant regenerated from NPJC6794 or any part thereof is also included in the present invention. The present invention additionally provides regenerated corn plants that express the genotype of NPJC6794 and/or manifest its phenotype, as well as mutants and/or variants thereof.

F. Transgenic Plants and/or Parts Thereof of Inbred Corn Line NPJC6794

The inbred corn line NPJC6794 comprising at least one transgene adapted to give NPJC6794 additional and/or altered phenotypic traits is a further aspect of the invention. Such transgenes are often associated with regulatory elements (promoters, enhancers, terminators and the like). As described above, transgenes that can be incorporated into a plant of this invention include, but are not limited to, insect resistance, herbicide resistance, disease resistance, increased or decreased starch or sugars or oils, lengthened or shortened life cycle or other altered trait, in any combination.

In some embodiments, the present invention provides inbred corn line NPJC6794 expressing at least one transgene or nucleotide sequence adapted to give NPJC6794 modified starch traits. Further provided is the inbred corn line NPJC6794 expressing at least one mutant gene adapted to give modified starch, fatty acid or oil traits, i.e., amylase, waxy, amylose extender or amylose.

The present invention additionally provides the inbred corn line NPJC6794 and at least one transgenic gene, which can be, but is not limited to, a nucleotide sequence encoding a *Bacillus thuringiensis* toxin, a nucleotide sequence encoding phosphinothricin acetyl transferase (e.g., bar or pat), a nucleotide sequence encoding Gdha, a nucleotide sequence encoding GOX, a nucleotide sequence encoding VIP, a nucleotide sequence encoding EPSP synthase, a nucleotide sequence encoding for low phytic acid production, or a nucleotide sequence encoding zein, and any combination thereof. In further embodiments, the present invention provides the inbred corn line NPJC6794 expressing at least one transgenic gene useful as a selectable marker or a screenable marker, as are well known in the art.

G. Genotyping and Marker Profiles

A number of well known methods can be employed to identify the genotype of a maize plant. One of the oldest methods is the use of isozymes, which provides a generalized footprint of the genetic material. Other approaches adapted to provide a higher definition profile include restriction fragment length polymorphisms (RFLPs), amplified fragment length polymorphisms (AFLPs), random amplified polymorphic DNAs (RAPDs), amplification methods such as the polymerase chain reaction (PCR), which can employ different types of primers or probes, microsatellites (SSRs), single nucleotide polymorphisms (SNPs), sequence selection markers, etc. as are well known in the art and can be found in standard textbooks such as *Breeding Field Crops*, Milton et. al. Iowa State University Press.

The marker profile of the inbred of this invention should be close to homozygous for alleles. A marker profile produced with any of the locus identifying systems known in the industry will identify a particular allele at a particular locus. An F1 hybrid made from the inbred of this invention will comprise a marker profile of the sum of both of the profiles of its inbred parents. At each locus, the allele for the inbred of the present invention and the allele for the other inbred parent should be present. Thus the profile of the inbred of the present invention allows for identification of hybrids as containing the inbred parent of the present invention. To identify the female portion of any hybrid, the hybrid seed material from the pericarp, which is maternally inherited, is employed in a marker technique. The resultant profile, therefore, is of the maternal parent. A comparison of this maternal profile with the hybrid profile will allow the identification of the paternal profile. Accordingly, some embodiments of the present invention provide an inbred or hybrid plant, plant part thereof, including but not limited to a seed or an embryo, and/or a cell thereof having the allele marker profile of the inbred plant of the this invention, NPJC6794.

Marker profiles of plants of this invention can be employed to identify essentially derived varieties or progeny developed with the inbred in its ancestry. The progeny of the inbred line of this invention, NPJC6794, can be identified by identifying in the progeny the molecular marker profile of the inbred line NPJC6794, as measured by either percent identity or percent similarity.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Therefore, as used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and Sequence Analysis Primer (Gribskov, M. and Devereux, J., eds.) Stockton Press, New York (1991).

As described herein, marker systems are not just useful for identification of the plants of this invention, but can also be used for breeding and trait conversion techniques. Polymorphisms in maize permit the use of markers for linkage analysis. If SSR are employed with flanking primers, the marker profile can be developed with PCR, and therefore Southern blots can often be eliminated. Use of flanking markers, PCR and amplification to genotype maize is well known in the art. Primer sequences for SSR markers and maize genome mapping information are publicly available on the USDA website at the Maize Genomics and Genetic Database (Maize GDB).

H. Production of Treated Seed

The present invention encompasses a method of producing treated hybrid or inbred seed of the plants of the present invention and the resultant treated seed. The method includes obtaining seed and treating the seed to improve its performance. Hybrid and inbred seed is often treated with one or more of the following including, but not limited to, fungicides, herbicides, herbicidal safeners, fertilizers, insecticides, acaricides, nematocides, bactericides, virus resistant material and/or other biocontrol agents. Pyrethrins, synthetic pyrethroids, oxadizine derivatives, chloronicotinyls, nitroguanidine derivatives and triazoles, organophosphates, pyrrols, pyrazoles, phenyl pyrazoles, diacylhydrazines, biological/fermentation products, carbamates and the like are used as pesticidal seed treatments. Additionally, fludioxonil, mefenoxam, azoxystrobin, thiamethoxam, clothianidin and the like are frequently used to treat maize seed. Methods for treating seed include but are not limited to the use of a fluidized bed, a roller mill, a rotostatic seed treater. a drum coaster, misting, soaking, filming coating and the like, in any combination. These methods of seed treatment are well known in the industry.

I. Maize as Human Food and Livestock Feed

Maize is used as human food, livestock feed and as raw material in industry. Sweet corn kernels having a relative moisture of approximately 72% are consumed by humans and may be processed by canning or freezing. The food uses of maize, in addition to human consumption of maize kernels, include both products of dry- and wet-milling industries. The principal products of maize dry milling are grits, meal and flour. The maize wet-milling industry can provide maize starch, maize syrups and dextrose for food use. Maize oil is recovered from maize germ, which is a by-product of both dry- and wet-milling industries.

The present invention further encompasses a hybrid plant with a plant part being the segregating grain formed on the ear of the hybrid. This grain is a commodity plant product as are the protein concentrate, protein isolate, starch, meal, flour or oil. A number of different industrial processes can be employed to extract or utilize these plant products, as are well known in the art.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The seed of the plant of the present invention can further comprise one or more single gene traits. The plant produced from the inbred seed of the maize line NPJC6794, the hybrid maize plant produced from the crossing of said inbred, hybrid seed and various parts of the hybrid maize plant, can be utilized for human food, livestock feed, and as a raw material in industry.

The present invention therefore also provides an agricultural product comprising a plant of the present invention or derived from a plant of the present invention. The present invention further provides an industrial product comprising a plant of the present invention or derived from a plant of the present invention. Additionally provided herein are methods of producing an agricultural and/or industrial product, the methods comprising planting seeds of the present invention, growing plant from such seeds, harvesting the plants and/or processing them to obtain an agricultural or industrial product. In some embodiments, the present invention provides a method of producing a commodity plant product comprising growing the plant from the seed of this invention or a part thereof and producing said commodity plant product, wherein said commodity plant product includes, but is not limited to, a protein concentrate, a protein isolate, starch, meal, flour, oil, or any combination thereof.

DEPOSIT INFORMATION

A deposit of at least 2500 seeds of inbred corn line NPJC6794 will be maintained by Syngenta Seeds Inc. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The ATCC number of the deposit is PTA-12400. The date of deposit was Jan. 12, 2012, and the seed was tested on Jan. 30, 2012 and found to be viable. The deposit of at least 2500 seeds will be from inbred seed taken from the deposit maintained by Syngenta Seeds Inc. The ATCC deposit will be maintained in that depository, which is a public depository, for a period of 30 years, or 5 years after the last request, or for the enforceable life of the patent, whichever is longer, and will be replaced if it becomes nonviable during that period.

Additional public information on patent variety protection may be available from the PVP Office, a division of the U.S. Government.

VARIETY DESCRIPTION INFORMATION
TABLE 1

NPJC6794
Variety Description Information
1 Type: Dent

2 Region Best Adapted:—Central

| *MG Group | Maturity Range | Hybrid RM* (estimate) |
|---|---|---|
| 6 | 108-112 | 110 |

*MG = Maturity group
**Maturity is the number of days from planting to physiological maturity (planting to black layer)
*** RM = relative maturity

3.

| Line | AntherColor | GlumeColor | SilkColor | BraceRootColor | CobColor | KernelColor | Endosperm Type |
|---|---|---|---|---|---|---|---|
| NPJC6794 | tan | light green | Light green | Absent | pink | Yellow | Normal |
| Inbred1 | Yellow | Green | Yellow | Faint | White | Yellow | |
| Inbred2 | Yellow | green | Yellow | Absent | Red | Yellow | Normal |

The data provided above is often a color. The Munsell code is a reference book of color, which is known and used in the industry and by persons with ordinary skill in the art of plant breeding. The purity and homozygosity of inbred NPJC6794 is constantly being tracked using isozyme genotypes. Isozyme data can be generated for inbred corn line NPJC6794 according to procedures known and published in the art.

Isozyme Genotypes for NPJC6794

Isozyme data were generated for inbred corn line NPJC6794 according to procedures known and published in the art. The data in the Electrophoresis Table gives the electrophoresis data on NPJC6794.

| ELECTROPHORESIS RESULTS FOR NPJC6794 | | | | | | | | | | | |
|---|---|---|---|---|---|---|---|---|---|---|---|
| Line | PGM1 | PGM2 | PGD1 | PGD2 | IDH1 | IDH2 | MDH1 | MDH2 | MDH3 | MDH4 | MDH5 |
| NPJC6794 | 9 | 4 | 3.8 | 5 | 4 | 4 | 6 | 3 | 16 | 12 | 12 |
| Inbred1 | 9 | 4 | 3.8 | 5 | 4 | 4 | 6 | 6 | 16 | 12 | 12 |
| Inbred2 | 9 | 4 | 3.8 | 5 | 4 | 4 | 6 | 3 | 16 | 12 | 12 |

| Line | MDH6 | ACP1 | ACP4 | PHI | ADH |
|---|---|---|---|---|---|
| NPJC6794 | Mm | 4 | 4 | 4 | 4 |
| Inbred1 | Mm | 4 | 3 | 4 | 4 |
| Inbred2 | Mm | 2 | 4 | 4 | 4 |

The Paired Inbred Comparison Data Table A show a comparison between NPJC6794 and comparable inbreds.

Paired Inbred Comparison Data Table A

| Inbred | Yield | Stand | HeatUnits to P50 | HeatUnits to S50 | Plant Height | Ear Height |
|---|---|---|---|---|---|---|
| NPJC6794 | 95.1 | 35333.3 | 1488.8 | 1526.4 | | |
| Inbred1 | 79.1 | 35416.7 | 1467 | 1491.9 | | |
| Diff | 16 | 83.3 | 21.8 | 34.5 | | |
| # Expts | 6 | 6 | 28 | 28 | | |
| Prob | 0.201 | 0.945 | 0.054* | 0.001*** | | |

-continued

| Inbred | % Large Rounds | % Large Flats | % Med. Rounds | % Med. Flats | % Small Rounds | % Small Flats | Shed Duration | Pollen Count |
|---|---|---|---|---|---|---|---|---|
| NPJC6794 | 7.2 | 8.1 | 37.4 | 42.7 | 1.6 | 1.9 | 257 | 1171215.4 |
| Inbred1 | 16.5 | 17.5 | 28.9 | 30 | 0.8 | 1.7 | 272.5 | 2478428.5 |
| Diff | 9.3 | 9.4 | 8.4 | 12.7 | 0.7 | 0.2 | 15.5 | 1307213.1 |
| # Expts | 6 | 6 | 6 | 6 | 6 | 6 | 4 | 8 |
| Prob | 0.001*** | 0.002*** | 0.034** | 0.017** | 0.146 | 0.682 | 0.586 | 0.001*** |

*.05 < Prob <= .10
**.01 < Prob <= .05
***.00 < Prob <= .01

In Paired Inbred Comparison Data Table B NPJC6794 shows a comparison for traits like yield, pollination, heat and silking heat units when compared with the other inbred.

The General Combining Ability Table shows the GCA (General Combining Ability) estimates of NPJC6794 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from our company's and other companies' hybrids which are commercial products and pre-commercial hybrids, which were grown in the same sets and locations.

| Line in hybrid combination | N | Yield | Moisture | TestWeight | % Stalk Lodging | % Push Test | % Late Root Lodging | % Early Root Lodging | % Dropped Ears | Final Stand |
|---|---|---|---|---|---|---|---|---|---|---|
| NPJC6794 | 4 | — | 0.64 | | −9.31 | | 20 | | | 0 |
| NPJC6794 | 13 | −5 | 1.12 | 1.18 | 0.58 | | 20 | | | −0.69 |
| NPJC6794 | 7 | −5.06 | 0.83 | 0.89 | −0.54 | | 0 | | | 0 |
| NPJC6794 | 26 | −1.86 | 1.07 | −1.32 | −1.09 | | 7.36 | 0 | | −0.23 |
| NPJC6794 | 10 | −9.15 | −4.3 | −2.05 | 0 | | | −19.66 | | −1.3 |
| NPJC6794 | 24 | 9.33 | 0.04 | −0.24 | −1.97 | 5.09 | −2.01 | 0.81 | | 0.45 |
| NPJC6794 | 113 | −3.04 | −0.5 | −0.38 | −1.18 | −10.57 | 0.65 | 11.62 | −0.17 | −6.32 |
| NPJC6794 | 11 | 12.31 | −2.12 | −1.57 | −2.45 | | 7.5 | | | 0 |
| NPJC6794 | 12 | 1.6 | −4.78 | −1.48 | −1.67 | | | 0.68 | | 0 |
| NPJC6794 | 34 | −0.16 | −0.5 | 0.19 | 0.05 | 38.33 | 7.8 | 0 | 0.63 | 0.06 |
| NPJC6794 | 25 | — | 1.73 | −0.19 | 1.54 | | 5.45 | 0 | | −0.13 |
| NPJC6794 | 30 | 9.02 | −0.52 | −0.7 | −1.12 | 2.86 | −15.15 | −27.15 | | −0.09 |
| NPJC6794 | 11 | — | 0.42 | −0.26 | 0.99 | | | | | 0.42 |
| NPJC6794 | 12 | 11.46 | 0.79 | −0.98 | −2.73 | | | | | 0.43 |
| NPJC6794 | 11 | 1.42 | −1.56 | −0.72 | −8.19 | | −9 | | | 0 |
| NPJC6794 | 10 | 15.75 | 1.92 | −0.33 | −0.45 | | 2.16 | | 0.26 | 0.1 |
| NPJC6794 | 7 | 10.16 | −3.33 | −1.52 | | | | −18.64 | | 0 |
| NPJC6794 | 26 | 1.37 | 0.44 | 1.06 | −0.64 | 0 | 8.17 | 7.04 | | −0.86 |
| NPJC6794 | 10 | 6.9 | −1.47 | −0.49 | −12.86 | | −55 | | | 0.08 |
| NPJC6794 | 9 | −7.05 | −3.93 | −1.76 | 0 | | | −7.8 | | 0 |
| NPJC6794 | 13 | 2.47 | 0.26 | 1.69 | 1.08 | | | | | 0 |
| NPJC6794 | 12 | −1.44 | −1.69 | −0.26 | 0 | | 7.46 | | | 0 |
| NPJC6794 | 7 | 8.73 | −0.76 | 0.17 | −0.92 | | | | | 0.34 |
| NPJC6794 | 13 | 7.13 | 0.08 | −0.09 | −6.13 | | | | | 0 |
| NPJC6794 | 13 | 11.95 | 0.58 | −0.77 | 0.59 | | | | | 0 |
| NPJC6794 | 13 | 9.01 | 1.32 | 0.77 | 1.48 | | | | | 0 |
| NPJC6794 | 13 | −4.12 | 1.4 | 0.75 | −0.68 | | | | | 0 |
| NPJC6794 | 13 | 10.18 | −1.45 | 0.82 | −1.08 | | 1.94 | | | 0.52 |
| NPJC6794 | 33 | 2.73 | −0.55 | 0.36 | −1.38 | 38.33 | 5.07 | −2.71 | 0.63 | −0.87 |
| NPJC6794 | 12 | 11.93 | −0.27 | −1.29 | 0.68 | | | | | 0 |
| NPJC6794 | 11 | 10.24 | −1.49 | −0.03 | 0.43 | | 2.5 | | | 0 |
| NPJC6794 | 46 | 6.83 | −1.12 | −1.06 | −1.78 | 22.17 | −5.28 | 5.98 | 0.63 | −1.99 |
| NPJC6794 | 12 | 2.7 | 0.63 | 0.4 | −5.06 | | | | | 0 |
| NPJC6794 | 10 | 17.35 | −0.56 | −1.43 | −0.48 | | 2.16 | | 0.26 | 0.3 |
| NPJC6794 | 13 | 12.86 | −0.18 | 1.42 | 2.02 | | | | | 0 |
| NPJC6794 | 8 | 20.74 | −2.38 | | −0.09 | | | | | 0 |
| NPJC6794 | 10 | — | −0.16 | 1.32 | −1.6 | | −5 | | | 0 |
| NPJC6794 | 14 | 15.8 | −1.04 | −0.48 | −0.43 | | 1.28 | | | 1.77 |
| NPJC6794 | 17 | −9.14 | 1.16 | −0.16 | 0.17 | | 0 | | | 0 |
| NPJC6794 | 52 | 11.25 | −0.86 | −0.55 | −0.27 | 24.29 | −0.07 | 0.15 | −0.5 | −0.08 |
| NPJC6794 | 13 | 7.3 | −0.6 | 0.12 | 1.32 | | 0.22 | | | −1.57 |
| NPJC6794 | 11 | −8.99 | −0.58 | −0.71 | 1.52 | | 0 | | | 0 |
| NPJC6794 | 13 | −2.84 | −0.17 | −0.09 | 2.45 | | 1.73 | | | −1.65 |
| NPJC6794 | 12 | 2.64 | 0.29 | 0.45 | 0.72 | | 2.03 | | | 0.71 |
| NPJC6794 | 13 | −7.77 | 0.89 | 0.89 | −6.34 | | | | | 0 |
| NPJC6794 | 8 | 3.88 | −2.26 | | 1.88 | | | | | 0 |
| NPJC6794 | 36 | 8.07 | −1.36 | 1.86 | −26.68 | | 0.58 | | | −1.26 |

-continued

| | | | | | | | | | |
|---|---|---|---|---|---|---|---|---|---|
| NPJC6794 | 11 | 11.63 | −2.37 | −0.35 | −1.98 | | −5 | | 0 |
| NPJC6794 | 9 | 13.49 | −1.19 | −0.1 | −0.04 | | 2.16 | 0.26 | 0.22 |
| NPJC6794 | 12 | — | 0.02 | −1.12 | 2.4 | | −11.9 | | −2.29 |
| NPJC6794 | 13 | 4.64 | −0.22 | 0.06 | 0.91 | | −0.24 | 8.67 | −1.19 |
| NPJC6794 | 11 | −0.37 | 0.62 | 0.62 | −0.28 | | −10 | | 0 |
| NPJC6794 | 61 | 8.68 | −0.15 | −0.75 | 0.26 | 19.05 | 1.15 | 2.99 | 0.21 | 0.43 |
| NPJC6794 | 29 | 3.04 | −1.16 | −0.06 | 0.5 | 1.43 | 5.09 | 0 | | 0.61 |
| NPJC6794 | 11 | 4.47 | −1.41 | 0.56 | −1.5 | | 0 | | 0 |
| NPJC6794 | 24 | −7.94 | 0.22 | 0.28 | −0.5 | | 3.98 | 0.15 | 0.27 |
| NPJC6794 | 23 | 4.36 | −0.43 | 0.86 | −2.28 | | 0 | | 0 |
| NPJC6794 | 33 | 4.07 | 1.14 | 1.12 | −1.4 | 20.73 | 1.52 | | −1.13 | −2.03 |
| NPJC6794 | 13 | 7.98 | 0.72 | 0.11 | −2.45 | | | | 0 |
| NPJC6794 | 20 | −2.52 | 0.84 | −0.47 | −0.93 | | 0 | 0 | 0 |
| NPJC6794 | 12 | 9.7 | −0.1 | 0.66 | 0.82 | | | | 0 |
| NPJC6794 | 13 | 9.16 | 0.04 | −0.28 | −2.15 | | | | 0 |
| NPJC6794 | 27 | 5.36 | −3.68 | −0.16 | −1.06 | | 8.17 | 0.34 | −0.12 |
| NPJC6794 | 5 | 11.77 | −0.34 | −0.53 | −4.55 | | | | −2.6 |
| NPJC6794 | 52 | 3.09 | 0.21 | 0.48 | 0.6 | 38.33 | 5.5 | 0 | −3.92 | −0.31 |
| NPJC6794 | 26 | 2.68 | −0.4 | −0.71 | 1.54 | | −15.57 | 0 | −0.13 |
| NPJC6794 | 10 | 5.79 | −0.73 | −0.45 | −4.69 | | −18.64 | 0.3 | 0.39 |
| NPJC6794 | 5 | — | −1.54 | | 0 | | | | 0.6 |
| NPJC6794 | 38 | 11.11 | −0.16 | 0.36 | −0.69 | 13.57 | 2.25 | 0 | 0.26 | 1 |
| NPJC6794 | 72 | 4.47 | −0.02 | 0.34 | −1.94 | −9.64 | 2.94 | 0.86 | 0.52 | 4.29 |
| NPJC6794 | 15 | −0.1 | −1.48 | 0.53 | 0.03 | | 5.71 | 0 | −0.09 |
| NPJC6794 | 36 | 6.57 | −0.25 | −1.47 | −0.19 | 12.86 | 1.32 | 0 | 0.16 |
| NPJC6794 | 11 | 3.98 | 1.51 | −0.07 | 0 | | −11.45 | 0.3 | 0.08 |
| NPJC6794 | 11 | 7.73 | −1.01 | 0.66 | −9.91 | | −30 | | 0 |
| NPJC6794 | 20 | −1.76 | 0.38 | 0 | 0.35 | | 0 | | 0 |
| NPJC6794 | 11 | 13.7 | −0.75 | −0.69 | −8.48 | | −15 | | 0 |
| NPJC6794 | 63 | 7.51 | −1.08 | −0.63 | 0.24 | 18.57 | 2.32 | 5.02 | 0.21 | 0.25 |
| NPJC6794 | 11 | 1.35 | 2.01 | 0.14 | −7.01 | | 2.81 | | 0 | 1.03 |
| NPJC6794 | 10 | 15.81 | −0.5 | −0.17 | −0.46 | | −4.27 | | 0.26 | 0.2 |
| NPJC6794 | 39 | 10.35 | −0.73 | −0.17 | −0.2 | 20.28 | −9.93 | 0.81 | 0.63 | −0.56 |
| NPJC6794 | 10 | −7.75 | −0.35 | 0.3 | 1.08 | | 1.73 | | 0 |
| NPJC6794 | 13 | −2.41 | −1.38 | −0.13 | 1.38 | | 2.18 | | 0.2 |
| NPJC6794 | 13 | −3.58 | −1.13 | −0.25 | 0.83 | | 1.98 | | 0.27 |
| NPJC6794 | 13 | 13.28 | −0.16 | −0.97 | 1.38 | | −8.87 | −8.33 | 0.12 |
| NPJC6794 | 13 | 3.34 | 0.4 | −0.14 | 0.35 | | 3.59 | | −0.49 |
| NPJC6794 | 9 | −6.31 | −0.72 | 1.27 | 0 | | 30 | 0 | −0.22 |
| NPJC6794 | 68 | 12.83 | −1.66 | −0.77 | 0.85 | 5.71 | 2.22 | 8.05 | 0.26 | 0.15 |
| NPJC6794 | 34 | 0.47 | −1.34 | 1.32 | 0.57 | | 17.13 | −0.25 | −0.17 |
| NPJC6794 | 15 | −0.25 | −0.71 | −0.56 | 1.5 | | 4.03 | 0 | −0.36 |
| NPJC6794 | 24 | −2.26 | −2.38 | 0.14 | 0.51 | | 2.47 | 0 | 0.11 |
| NPJC6794 | 37 | 4.19 | 0.19 | 0.81 | 0.96 | 24.29 | −1.33 | −8.25 | 0.26 | 0.47 |
| NPJC6794 | 32 | 1.3 | −1.08 | −0.66 | 0.59 | | 4.24 | −0.5 | −0.15 |
| NPJC6794 | 10 | −1.16 | 1.49 | 0.61 | 0 | | −20.41 | −4.7 | −0.11 |
| NPJC6794 | 9 | −0.66 | −1.73 | 1.01 | 0 | | 30 | 0 | −0.22 |
| NPJC6794 | 9 | 9.86 | −1.29 | −0.15 | 0 | | −16.67 | 0 | 0.33 |
| NPJC6794 | 11 | 1.98 | 0.05 | 0.18 | 0 | | −6.61 | 0.3 | 0.45 |
| NPJC6794 | 11 | 4.64 | 0.12 | 0.1 | 0 | | −6.61 | 0.3 | 0.63 |
| NPJC6794 | 14 | 9.26 | −2.44 | −0.16 | −0.75 | | 8.17 | 0 | −0.74 |
| NPJC6794 | 10 | 6.57 | 0.93 | 0.53 | 0.4 | | −10.8 | | 0.26 | 0.3 |
| NPJC6794 | 11 | 0.91 | −0.69 | 2.11 | 0.66 | | | | 0.31 |
| NPJC6794 | 10 | 3.53 | 0.41 | 0.7 | 2.95 | | | | 0.34 |
| NPJC6794 | 11 | 16.5 | −3.79 | | 1.95 | | | | −1.18 |
| NPJC6794 | 12 | 5.86 | −1.67 | −0.04 | 1.95 | | | | 0 |
| NPJC6794 | 11 | 0.28 | −1.94 | 0.24 | 1.25 | | 1 | | 0 |
| NPJC6794 | 10 | 7.72 | −0.57 | 0.49 | −0.63 | | | | 0.34 |
| NPJC6794 | 9 | 0.45 | −1.29 | 0.45 | 1.06 | | | | 0.38 |
| NPJC6794 | 12 | −3.91 | −4.05 | −0.04 | 0 | | | −41.69 | −1.08 |
| NPJC6794 | 9 | −4.47 | −0.65 | −0.3 | 1.43 | | −5 | | 0.08 |
| NPJC6794 | 14 | 4.24 | −0.88 | 1.01 | −1.42 | | 2.11 | | 1.99 |
| NPJC6794 | 11 | −7.51 | −0.67 | 0.46 | 0.95 | | | | 0.31 |
| NPJC6794 | 12 | 7.14 | −1.22 | | −6.95 | | | | 0 |
| NPJC6794 | 10 | 15.09 | −2.57 | | −0.79 | | | | 0 |
| NPJC6794 | 12 | 2.58 | −3.9 | −1.53 | 0 | | | −36.61 | 0 |
| NPJC6794 | 11 | −3.28 | −1.2 | 0.57 | 1.81 | | | | 0.31 |
| NPJC6794 | 10 | — | −1.62 | 0.66 | 0.07 | | | | 0.34 |
| NPJC6794 | 10 | −1.99 | −1.66 | −0.13 | 0.82 | | | | 0.34 |
| NPJC6794 | 10 | −0.3 | −0.25 | 0.04 | 1.87 | | 0.69 | | 0.26 | 0 |
| NPJC6794 | 10 | 13.68 | 0.71 | −0.35 | −2.85 | | −14.37 | | 0.26 | −0.1 |
| NPJC6794 | 6 | −7.29 | −1 | 0.2 | 0.41 | | 0.95 | | −0.58 |
| NPJC6794 | 7 | 18.31 | −1.18 | | 0.58 | | | | −3.14 |
| NPJC6794 | 11 | −1.43 | −1.24 | 1.06 | 2.88 | | | | 0.31 |
| NPJC6794 | 12 | 13.63 | 0.24 | −1.14 | 6.73 | | −2.08 | | −0.63 |
| NPJC6794 | 9 | — | −2.18 | −0.13 | 0.58 | | | | 0.38 |
| NPJC6794 | 10 | 7.3 | −0.23 | 0.31 | −2.54 | | 2.16 | | 0.14 | 0.1 |
| NPJC6794 | 10 | 6.24 | 0.3 | −0.45 | 5.37 | | 2.92 | | 0.17 |
| NPJC6794 | 13 | 7.98 | −0.44 | −0.99 | 0.77 | | 1.73 | | 0.12 |
| NPJC6794 | 11 | −2.31 | 0.56 | −1.98 | −0.01 | | −5 | | 0 |

-continued

| | | | | | | | | | |
|---|---|---|---|---|---|---|---|---|---|
| NPJC6794 | 6 | 16.01 | 0.71 | 0.28 | −1.89 | | 2.38 | | 0.25 |
| NPJC6794 | 7 | 16 | 0.18 | 0.07 | −4.19 | | −5.84 | | 0 |
| NPJC6794 | 10 | −2.38 | −0.56 | 0.63 | −0.23 | | 2.81 | 0 | 0.83 |
| NPJC6794 | 11 | −9.55 | −2.02 | −0.98 | −2.71 | | −25 | | 0 |
| NPJC6794 | 11 | −2.26 | −2.64 | 0.25 | −0.25 | | −7.51 | 0 | −0.79 |
| NPJC6794 | 10 | 0.21 | −0.7 | −0.5 | −4.62 | | −1.85 | | −2.9 |
| NPJC6794 | 10 | 11.38 | −2.69 | −2.51 | 7.14 | | −10.19 | | 0 |
| NPJC6794 | 9 | 20.32 | −0.5 | −0.18 | 4.2 | | −0.46 | | 0 |
| NPJC6794 | 7 | −1.9 | −2.26 | −1.55 | 3.37 | | −0.46 | | — |
| NPJC6794 | 9 | — | 1.31 | −0.17 | −1.68 | | 2.31 | | 0 |
| NPJC6794 | 9 | 21.48 | −1.85 | −1.84 | −7.56 | | 2.31 | | 0 |
| NPJC6794 | 9 | −1.35 | −0.95 | −0.65 | 1.26 | | 2.31 | | 0 |
| NPJC6794 | 10 | 0.64 | −1.55 | −1.48 | 1.26 | | 2.31 | | 0 |
| NPJC6794 | 10 | 4.06 | −2.17 | −2.26 | 1.26 | | −24.07 | | 0 |
| NPJC6794 | 10 | 19.98 | −4.19 | −4.01 | −1.68 | | 2.31 | | 0 |
| NPJC6794 | 10 | 12.13 | −3.14 | −1.44 | −10.5 | | 2.31 | | 0 |
| NPJC6794 | 10 | −8.66 | −0.2 | 0.77 | −4.62 | | −8.8 | | 0 |
| NPJC6794 | 10 | 16.93 | −1.66 | −2.2 | 4.2 | | 2.31 | | 0 |
| NPJC6794 | 10 | −9.52 | −0.48 | −0.6 | 4.2 | | −8.8 | | 0 |
| NPJC6794 | 10 | 7.95 | −2.53 | −2.91 | −1.68 | | −24.07 | | −1.1 |
| NPJC6794 | 9 | 12.03 | −3.17 | −3.11 | 7.14 | | 2.31 | | 0 |
| NPJC6794 | 10 | 13.05 | −2.45 | −1.94 | −1.68 | | −24.07 | | 0 |
| NPJC6794 | 10 | 13.8 | −0.11 | −1.75 | 4.2 | | −10.19 | | 0 |
| NPJC6794 | 7 | 12.3 | −1.38 | −2.84 | −1.68 | | −0.46 | | −2.14 |
| NPJC6794 | 11 | −6.5 | −1.16 | 0.58 | 2.79 | 21 | | | −1.36 |
| NPJC6794 | 10 | 18.91 | −2.87 | −2.83 | 1.26 | | 2.31 | | 0 |
| NPJC6794 | 9 | −7.93 | 0 | −3.52 | −1.68 | | 2.31 | | 0 |
| NPJC6794 | 7 | −3.66 | −1.34 | −1.33 | −10.5 | | −7.41 | | 0 |
| NPJC6794 | 10 | −4.23 | 0.17 | −0.52 | 1.26 | | −40.74 | | 0 |
| NPJC6794 | 9 | — | −1.5 | −2.05 | 3.63 | | −6.02 | | −4.67 |
| NPJC6794 | 10 | 10.83 | −2.77 | −1.82 | −16.39 | | −22.69 | | 0 |
| NPJC6794 | 10 | 24.23 | −2.93 | −2.78 | −4.62 | | −0.46 | | 0 |
| NPJC6794 | 9 | 27.21 | −2.82 | −3.88 | −1.68 | | −6.02 | | 0 |
| NPJC6794 | 9 | 13.95 | −2.62 | −2.89 | 1.26 | | 2.31 | | 0 |
| NPJC6794 | 10 | −3.99 | −1.88 | −1.64 | −10.5 | | 2.31 | | 0 |
| NPJC6794 | 10 | 18.87 | −3.15 | −2.8 | −1.68 | | −17.13 | | 0 |
| NPJC6794 | 10 | 14.04 | −1.58 | −1.13 | 7.14 | | 2.31 | | 0 |
| NPJC6794 | 10 | 13.73 | −2.14 | −2.69 | −1.68 | | 2.31 | | 0 |
| NPJC6794 | 9 | 9.07 | −1.56 | −2.99 | 1.26 | | −0.46 | | 0 |
| NPJC6794 | 10 | 19.04 | −1.36 | −2.11 | 4.2 | | 2.31 | | 0 |
| NPJC6794 | 9 | 7.39 | −1.26 | −2.53 | 1.26 | | 2.31 | | 0 |
| NPJC6794 | 9 | 10.84 | −2.38 | −2.58 | −1.68 | | 2.31 | | 0 |
| NPJC6794 | 10 | 7.69 | −2.82 | −2.26 | −7.56 | | 2.31 | | 0 |
| NPJC6794 | 9 | 5.81 | −1.23 | −2.65 | −1.68 | | 2.31 | | 0 |
| NPJC6794 | 10 | 10.39 | −1.64 | −2.42 | −7.56 | | 2.31 | | 0 |
| NPJC6794 | 9 | 18.04 | −1.25 | −0.79 | 1.26 | | 2.31 | | 0 |
| NPJC6794 | 9 | −4.59 | −2.34 | −3.13 | −1.68 | | −4.63 | | −1.56 |
| NPJC6794 | 10 | −4.81 | −2.11 | −1.95 | −4.62 | | −3.24 | | 0 |
| NPJC6794 | 10 | 4.31 | −0.58 | −1.71 | −7.56 | | −1.85 | | 0 |
| NPJC6794 | 10 | −7.34 | 0.76 | 0.3 | −1.68 | | 2.31 | | 0 |
| NPJC6794 | 11 | −7.2 | 0.77 | −1.92 | −1.19 | | 0 | | 0 |
| NPJC6794 | 32 | −8.33 | 1.72 | −0.07 | −0.22 | 24.29 | 0.94 | 0.26 | −0.93 |
| NPJC6794 | 10 | −17.3 | 1.72 | −0.01 | 0.78 | | −5 | | −2.2 |
| NPJC6794 | 10 | 2.32 | −0.23 | −0.31 | −0.16 | | −27.5 | | 0 |
| NPJC6794 | 11 | −9.1 | −0.07 | −0.82 | 0.02 | | 0 | | 0 |
| NPJC6794 | 11 | — | 3 | −2.34 | 0.34 | | −5 | | 0 |
| NPJC6794 | 48 | −0.9 | 0.58 | −0.62 | 0.08 | 22.17 | −7.33 | 6.65 | 0.63 | 0.55 |
| NPJC6794 | 29 | −8.77 | 1.47 | −0.75 | 1.03 | 18.57 | 0.08 | | 0.26 | −0.49 |
| NPJC6794 | 10 | 3.7 | −2.92 | 0.12 | −2.25 | | −12.5 | | 0 |
| NPJC6794 | 17 | −0.81 | 1.5 | −1.3 | −11.44 | −20 | −8.43 | 22.13 | 0 | 1.85 |
| NPJC6794 | 11 | −7.69 | 0.71 | −0.88 | 1.93 | | −5 | | 0 |
| NPJC6794 | 10 | −9.54 | 2.15 | −0.58 | 0.09 | | −10 | | 0 |
| NPJC6794 | 20 | 4.09 | 0.99 | −1.02 | −0.2 | −11.67 | 8.48 | | −0.72 | 1.41 |
| NPJC6794 | 9 | — | 2.91 | −1.62 | 1.71 | | −5 | | 0 |
| NPJC6794 | 10 | — | 1.11 | −1.77 | 1.84 | | −5 | | 0 |
| NPJC6794 | 11 | — | 2.01 | −2.48 | 1.46 | | −10 | | 0 |
| NPJC6794 | 46 | 1.84 | −0.25 | 0.07 | −0.53 | 22.17 | 7.76 | 8.56 | −0.86 | 1.17 |
| NPJC6794 | 29 | 5.64 | −0.67 | 0.16 | −0.28 | 18.33 | 8.99 | | 0.63 | −0.95 |
| NPJC6794 | 11 | — | 2.52 | −0.77 | −0.64 | | 0 | | 0 |
| NPJC6794 | 11 | — | 1.38 | −1.02 | 1.15 | | 0 | | 0 |
| NPJC6794 | 11 | — | 1.83 | −0.31 | 0.83 | | 0 | | −0.91 |
| NPJC6794 | 10 | — | 0.51 | 0.7 | −1.69 | | 0 | | 0 |
| NPJC6794 | 11 | — | 1.73 | 0.56 | 0.41 | | 0 | | 0 |
| NPJC6794 | 30 | 2.82 | −0.07 | −0.25 | −0.14 | 38.33 | 7.53 | | 0.63 | 0.12 |
| NPJC6794 | 23 | 8.15 | 0.19 | 0.28 | −0.3 | | 8.57 | | 0.26 | 1.85 |
| NPJC6794 | 34 | 2.17 | 0.29 | −0.21 | −1.65 | −56.43 | −0.1 | 0.5 | −0.46 | 0.52 |
| NPJC6794 | 23 | −1.22 | −0.25 | 0.36 | −0.81 | −51.43 | −0.23 | | 0.26 | 1.62 |
| NPJC6794 | 63 | 4.13 | 0.45 | 0.02 | 0.07 | 5.71 | 0.96 | 21.33 | 0.09 | 0.31 |
| NPJC6794 | 11 | 13.48 | −1.58 | −0.35 | −1.53 | | 5 | | 0 |
| NPJC6794 | 10 | 7.36 | −1.09 | −0.07 | −5.01 | | −7.5 | | −1.4 |

-continued

| | | | | | | | | |
|---|---|---|---|---|---|---|---|---|
| NPJC6794 | 6 | — | −0.68 | −0.27 | −2.32 | 0 | | −2 |
| NPJC6794 | 11 | 4.59 | −1.34 | −0.02 | −1.13 | −5 | | 0 |
| NPJC6794 | 10 | 2.68 | −1.12 | −0.26 | −2.11 | 5 | | −1 |
| NPJC6794 | 10 | — | −2.01 | −0.33 | −2.08 | 0 | | −1.4 |
| NPJC6794 | 11 | 0.74 | 0.43 | 0.22 | −8.53 | 0 | | 0 |
| NPJC6794 | 13 | 29.03 | −0.69 | 0.22 | −0.62 | −21.6 | | 0.52 |
| NPJC6794 | 11 | 2.59 | −1.34 | −0.46 | −10.62 | −22.5 | | 0 |
| NPJC6794 | 11 | 9.71 | 1.5 | 0.19 | −9.99 | −10 | | 0 |
| NPJC6794 | 12 | 10.44 | −0.43 | −1.46 | −6.36 | 0.17 | | 0.56 |
| NPJC6794 | 11 | — | 0.19 | 0.42 | −3.67 | −27.5 | | 0 |
| NPJC6794 | 11 | 11.97 | −1.41 | −0.87 | 0.46 | −25 | | 0 |
| NPJC6794 | 11 | 15.65 | −3.44 | −1.55 | −1.53 | 7.5 | | 0 |
| NPJC6794 | 11 | 10.2 | −1.05 | −0.12 | −0.1 | −55 | | 0 |
| NPJC6794 | 11 | 10.42 | −2.23 | −0.1 | −4.05 | −27.5 | | 0 |
| NPJC6794 | 11 | 14.2 | −2.67 | −0.18 | −1.53 | −22.5 | | 0 |
| NPJC6794 | 10 | 22.03 | −1.78 | −0.61 | 0.91 | −16.71 | | 0.43 |
| NPJC6794 | 10 | 2.39 | 0.5 | −2.67 | −1.53 | −32.5 | | 0.43 |
| NPJC6794 | 9 | 25.45 | −1.03 | −2.11 | 0.25 | | | 0.48 |
| NPJC6794 | 10 | 13.23 | −0.33 | 0.8 | 1.29 | −3 | 0.26 | −0.2 |
| NPJC6794 | 9 | −2.46 | 0.12 | 0.93 | 1 | 2.16 | 0.26 | −0.11 |
| NPJC6794 | 9 | 27.5 | 0.1 | 0.56 | −3.02 | 2.16 | 0.26 | −0.44 |
| NPJC6794 | 9 | 11.85 | 0.88 | −0.08 | 0.98 | 1.39 | 0.26 | −0.44 |
| NPJC6794 | 11 | 10.79 | −0.67 | −0.87 | −4.38 | −7.5 | | 0 |
| NPJC6794 | 10 | 30.16 | −1.06 | −0.03 | 0.32 | 0 | | 0 |
| NPJC6794 | 11 | 9.57 | −1.19 | −0.6 | −2.93 | 7.5 | | 0 |
| NPJC6794 | 11 | 0.96 | −2.1 | 0.3 | −5.96 | −12.5 | | 0 |
| NPJC6794 | 11 | 3.28 | −1.78 | −0.57 | −1.56 | 7.5 | | 0 |
| NPJC6794 | 11 | 13.78 | −2.68 | −0.57 | −5.91 | −17.5 | | 0 |
| NPJC6794 | 11 | −1.73 | −2.42 | −0.77 | −6.05 | 7.5 | | 0 |
| NPJC6794 | 11 | 0.89 | −0.78 | −0.86 | −9.53 | −2.5 | | 0 |
| NPJC6794 | 11 | 16.37 | −2.56 | −0.12 | −1.53 | 0 | | 0 |
| NPJC6794 | 10 | 9.83 | −1.13 | −0.8 | −9.61 | −12.5 | | 0 |
| NPJC6794 | 11 | 7.85 | 0.29 | −0.96 | 0.93 | −22.5 | | 0 |
| NPJC6794 | 6 | 13.59 | 0.33 | 0.65 | 0.56 | 3.81 | | 0.25 |
| NPJC6794 | 8 | 3.06 | 0.03 | 0.09 | 0.63 | −1.41 | 0.26 | 0 |
| NPJC6794 | 11 | 1.5 | −3.19 | −0.86 | 1.81 | 31 | | 0 |
| NPJC6794 | 32 | 12.99 | −0.37 | −0.39 | −0.46 | 13.33 | −13.84 | 12.81 | 0 | −0.31 |
| NPJC6794 | 13 | 7.71 | −0.96 | −0.87 | 1.54 | −21.6 | | 0.52 |
| NPJC6794 | 11 | −0.47 | −1.89 | −0.07 | −3.04 | 11 | | 0 |
| NPJC6794 | 11 | 9.27 | −2.76 | −2.37 | −1.75 | 26 | | 0 |
| NPJC6794 | 10 | 12.84 | −2.56 | −0.38 | 0.83 | −9 | | 0 |
| NPJC6794 | 9 | −8.87 | 1.33 | 0.46 | 0.71 | 2.16 | 0.26 | 0.33 |
| NPJC6794 | 6 | 9.75 | 0.48 | 0.37 | −1.4 | 3.81 | | 0.08 |
| NPJC6794 | 10 | 11.98 | 1.07 | −1.16 | 0.71 | −6.05 | 0.26 | −0.6 |
| NPJC6794 | 10 | 13.55 | −0.4 | 0.45 | 0.7 | 2.16 | 0.26 | −0.3 |
| NPJC6794 | 10 | 10.32 | 1.17 | −0.11 | −1.92 | −2.84 | 0.26 | 0.2 |
| NPJC6794 | 10 | 7.39 | 0.59 | 0.69 | 1.29 | −3.56 | 0.26 | 0 |
| NPJC6794 | 11 | −3.57 | −0.2 | −1.84 | −1.13 | 6 | | 0 |
| NPJC6794 | 11 | 5.22 | −2.83 | −0.57 | −0.18 | 21 | | 0 |
| NPJC6794 | 11 | −1.17 | −0.93 | −1.6 | 2.26 | 21 | | 0 |
| NPJC6794 | 11 | 24.61 | −1.6 | −2.26 | 2.49 | 17.5 | | 0.39 |
| NPJC6794 | 9 | — | −1.18 | −0.36 | 5.7 | 26 | | 0 |
| NPJC6794 | 8 | — | −2.57 | −0.27 | 3.97 | 36 | | 0 |
| NPJC6794 | 10 | 16.2 | −1.27 | −0.54 | 0.93 | −5 | | 0 |
| NPJC6794 | 11 | 5.45 | −1.6 | −0.6 | −8 | 0 | | 0 |
| NPJC6794 | 11 | 7.73 | −0.75 | −1.12 | −6.26 | −22.5 | | 0 |
| NPJC6794 | 10 | 14.49 | 0 | −0.52 | 0.45 | 0.01 | 0.26 | 0.1 |
| NPJC6794 | 9 | 6.99 | 1.47 | 1.06 | −0.16 | −14.38 | 0.26 | −0.11 |
| NPJC6794 | 10 | 6.13 | 0.32 | −1.35 | 0.99 | −4.99 | −1.26 | −0.3 |
| NPJC6794 | 10 | 16.21 | 2.36 | −1.19 | 0.12 | −5.07 | 0.26 | 0.1 |
| NPJC6794 | 10 | 17.93 | 0.95 | 1.19 | −3.11 | −0.08 | 0.26 | 0.1 |
| NPJC6794 | 9 | 9.8 | 1.73 | 1.07 | 0.11 | 2.16 | 0.26 | 0.33 |
| NPJC6794 | 11 | −9.78 | −2.88 | −0.04 | −0.55 | −30 | | 0 |
| NPJC6794 | 10 | 12.75 | 1.65 | 1.25 | 0.1 | −3.56 | 0.26 | −0.5 |
| NPJC6794 | 10 | — | −0.67 | −0.69 | −23.71 | −5 | | −2.2 |
| NPJC6794 | 10 | 14.85 | 0.71 | 1.14 | −2.82 | 2.16 | 0.26 | 0.1 |
| NPJC6794 | 8 | −2.5 | 0.02 | −0.15 | −1.67 | −2.13 | 0.26 | −1.63 |
| NPJC6794 | 10 | 11.2 | 1.52 | 0.89 | −4.3 | 2.16 | 0.26 | −0.1 |
| NPJC6794 | 10 | 12.98 | −0.58 | 0.8 | −4.55 | −0.12 | 0.26 | 0.1 |
| NPJC6794 | 10 | 7.95 | 1.38 | −0.07 | −0.86 | 0.73 | 0.26 | −0.3 |
| NPJC6794 | 10 | 0.92 | 1.36 | 0.63 | 0.7 | 2.16 | 0.26 | 0.1 |
| NPJC6794 | 10 | 3.27 | 2.6 | 0.79 | −0.47 | −6.41 | 0.26 | −0.1 |
| NPJC6794 | 10 | 7.43 | 1.35 | 1.04 | 0.12 | 1.44 | 0.26 | 0.2 |
| NPJC6794 | 11 | 7.29 | −1.67 | −0.54 | 0.8 | −14 | | 0 |
| NPJC6794 | 7 | 7.86 | −1.83 | −1.15 | 3.26 | 21 | | 0 |
| NPJC6794 | 11 | 10.14 | −0.31 | −2.48 | −1.21 | −34 | | 0 |
| NPJC6794 | 10 | 2.81 | −2.6 | −1.26 | 6.01 | 6 | | 0 |
| NPJC6794 | 11 | 6.57 | −2.62 | 0.22 | 1.27 | −19 | | 0 |
| NPJC6794 | 11 | 1.94 | 0.49 | −0.9 | −0.35 | 16 | | 0 |
| NPJC6794 | 10 | — | 0.95 | −0.91 | −28.84 | 36 | | 0 |

-continued

| | | | | | | | | | |
|---|---|---|---|---|---|---|---|---|---|
| NPJC6794 | 11 | 6.03 | −0.61 | −0.6 | 3.24 | | −19 | | 0 |
| NPJC6794 | 11 | 9.84 | −0.78 | 0.44 | 0.35 | | −9 | | 0 |
| NPJC6794 | 10 | 7.64 | −3.09 | −1.07 | 0.13 | | 26 | | 0 |
| NPJC6794 | 10 | 5.74 | 1.54 | 1.54 | 1.87 | | 2.16 | 0.26 | 0.1 |
| NPJC6794 | 9 | 31.06 | 0.17 | 0.85 | 0.64 | | −0.97 | 0.26 | −0.22 |
| NPJC6794 | 10 | 19.99 | 2.17 | 1.26 | −3.97 | | 2.16 | 0.26 | 0.1 |
| NPJC6794 | 14 | 6.54 | −0.56 | 1.25 | −0.75 | | −2.06 | | 0.77 |
| NPJC6794 | 14 | −3.01 | 0.34 | 2.02 | −0.8 | | 2.11 | | 1.63 |
| NPJC6794 | 14 | 3.54 | 0.2 | 1.41 | −2.16 | | 3.78 | | 0.27 |
| NPJC6794 | 10 | 15.07 | −0.44 | −0.34 | 0.11 | | 2.16 | 0.26 | −0.1 |
| NPJC6794 | 14 | 7.45 | −0.73 | 1.77 | 0.49 | | 1.78 | | −0.73 |
| NPJC6794 | 14 | 21.01 | −2.57 | 0.9 | −0.35 | | 2.11 | | 1.56 |
| NPJC6794 | 8 | 8.32 | 0.44 | −0.13 | 3.82 | | | | 0.31 |
| NPJC6794 | 9 | 12.03 | 2.11 | 0.54 | −3.6 | | 2.16 | 0.26 | −0.11 |
| NPJC6794 | 17 | 6.52 | 1.14 | −1.09 | −8.23 | 4 | 0.58 | −12.87 | 0.57 |
| NPJC6794 | 14 | 15.66 | −0.08 | −0.69 | −1.24 | | 2.11 | | 0.77 |
| NPJC6794 | 14 | 11.25 | 1.01 | 1.59 | −1.16 | | 3.78 | | 0.06 |
| NPJC6794 | 18 | −3.71 | −0.46 | −0.38 | −5.37 | 4 | −7.62 | −4.82 | −2.37 |
| NPJC6794 | 14 | 24 | −0.6 | −1.07 | 0.25 | | 0.44 | | 1.27 |
| NPJC6794 | 14 | 3.36 | 0.24 | −0.09 | −1.58 | | −8.39 | | 0.06 |
| NPJC6794 | 14 | 24.57 | 0.24 | 0.57 | −1.5 | | −0.72 | | 1.42 |
| NPJC6794 | 10 | 2.5 | −0.63 | −0.47 | −2.14 | | 26 | | 0 |
| NPJC6794 | 14 | 4.22 | 0.86 | −0.11 | −1.98 | | 1.11 | | −0.3 |
| NPJC6794 | 13 | 0.93 | −1.13 | 1.55 | −2.02 | | −1.53 | | 0.88 |
| NPJC6794 | 14 | 10.09 | −0.51 | −0.47 | 0.53 | | −10.39 | | 0.85 |
| NPJC6794 | 14 | 18.16 | −0.05 | 1.18 | −0.76 | | 0.11 | | −0.51 |
| NPJC6794 | 10 | 9.7 | 1.78 | 0.46 | −6 | | 2.16 | 0.26 | −0.2 |
| NPJC6794 | 15 | 3.4 | −0.65 | −1.34 | −5.11 | 4 | 4.91 | 18.86 | −1.37 |
| NPJC6794 | 7 | — | 0.82 | 0.54 | −3.94 | 0 | 2.39 | 15.08 | — |
| NPJC6794 | 18 | 2.06 | 3.17 | −0.65 | −1.94 | 0 | 1.91 | 21.27 | 0.96 |
| NPJC6794 | 29 | 7.75 | −1.63 | −1.25 | −5.04 | 4 | −0.79 | 0.04 | −0.83 |
| NPJC6794 | 14 | 6.6 | 0.05 | −1.28 | −0.87 | | 1.94 | | 0.92 |
| NPJC6794 | 17 | 2.27 | 1.05 | −0.07 | 0.5 | 0 | 1.26 | 23.62 | 0.75 |
| NPJC6794 | 16 | 4.63 | 0.47 | −0.43 | 2.28 | 0 | −0.3 | 17.29 | 0.49 |
| NPJC6794 | 2 | — | −0.36 | −0.26 | | 0 | | −3.1 | — |
| NPJC6794 | 9 | 11.91 | 1.43 | 0.54 | 2.1 | | 2.16 | 0.26 | 0.22 |
| NPJC6794 | 18 | 3.01 | 1.32 | −0.57 | −3.71 | 0 | −3.52 | 21.99 | −1.42 |
| NPJC6794 | 14 | 21.55 | −1.05 | −1.17 | −0.93 | | 1.44 | | 1.2 |
| NPJC6794 | 18 | 7.09 | 1.77 | −0.3 | −2.33 | 0 | −6.22 | −5.95 | 0.58 |
| NPJC6794 | 10 | 6.16 | −0.52 | 0.01 | −0.18 | | 0.73 | 0.26 | 0.1 |
| NPJC6794 | 14 | 3.33 | 0.4 | 1.13 | −2.18 | | 3.44 | | 1.06 |
| NPJC6794 | 14 | 3.97 | 0 | −1.12 | −0.53 | | 1.78 | | 0.85 |
| NPJC6794 | 14 | 13.37 | 0.65 | 0.81 | −1.57 | | 0.94 | | 1.13 |
| NPJC6794 | 14 | 3.16 | 0.44 | −0.59 | 0.06 | | 1.28 | | 0.92 |
| NPJC6794 | 14 | 9.19 | −0.34 | −0.12 | −3.5 | | 2.11 | | 1.27 |
| NPJC6794 | 14 | −5.3 | −0.3 | −0.87 | 0.29 | | −9.89 | | 0.99 |
| NPJC6794 | 14 | 5.37 | 1.24 | −0.58 | −1.58 | | 1.28 | | 0.99 |
| NPJC6794 | 14 | 6.9 | −0.17 | 0.22 | −1.95 | | −13.56 | | 1.2 |
| NPJC6794 | 14 | 8.45 | −0.17 | −0.93 | −1.34 | | −9.89 | | 1.06 |
| NPJC6794 | 14 | 12.61 | 0.21 | −0.08 | −1.83 | | −7.39 | | 1.13 |
| NPJC6794 | 14 | 1.06 | −0.18 | 0.91 | 0.13 | | −3.39 | | −0.58 |
| NPJC6794 | 18 | 14.51 | −1.75 | 1.09 | 0.27 | | 1.59 | | −0.65 |
| NPJC6794 | 12 | 2.96 | −5.36 | −1.16 | 0 | | | −2.71 | 0 |
| NPJC6794 | 22 | 0.32 | 0.84 | −1.68 | −2.93 | | −10 | | 0.24 |
| NPJC6794 | 12 | −4.06 | −4.94 | −1.23 | 0 | | | 4.07 | 0 |
| NPJC6794 | 11 | — | 0.17 | −2.24 | 0.05 | | 0 | | 0 |
| NPJC6794 | 6 | 1.99 | −1.18 | −0.61 | 2 | | | | 0.31 |
| XR = | 4901 | 4.24 | −0.47 | −0.38 | −1.08 | 3.67 | −1.17 | 1.57 | 0.11 | −0.13 |
| XH = | 344 | 4.17 | −0.56 | −0.41 | −1.17 | 7.76 | −1.61 | −1.11 | 0.11 | −0.15 |
| XT = | 30 | 5.35 | −0.37 | −0.03 | −1.28 | 17.28 | 0.72 | 1.73 | −0.08 | −0.03 |

| Line in hybrid combination | Stay Green % | % Green Snap | % Barren | Emergence Rating | Vigor Rating | Heatunits to S50 | Heatunits to P50 | Ear Height | Plant Height |
|---|---|---|---|---|---|---|---|---|---|
| NPJC6794 | | | | | | | | | |
| NPJC6794 | | | | | | | | | |
| NPJC6794 | | | | | | | | | |
| NPJC6794 | | | | | | | | | |
| NPJC6794 | | | | | | 49.48 | | −16.67 | −4.17 |
| NPJC6794 | | −1.2 | | | −0.73 | 0.45 | 15.1 | −0.81 | 9.97 |
| NPJC6794 | −0.66 | 0.5 | 0 | 0.33 | 0.71 | 13.67 | −8.97 | 10.65 |
| NPJC6794 | | 0.88 | | | | | | −7.55 | 0.18 |
| NPJC6794 | | | | | | 74.73 | | −31.67 | −9.17 |
| NPJC6794 | 16.67 | −2.01 | | 0.88 | −1.5 | −4.6 | −9.43 | −7.5 | −9.67 |
| NPJC6794 | | −1.94 | | | | | | | |
| NPJC6794 | | −3.95 | | 0.29 | 0.49 | −20.64 | −6.36 | −1.2 | 17.29 |
| NPJC6794 | | 5.44 | | | | | | −1.5 | 8.5 |
| NPJC6794 | | 2.39 | | | | | | 9.5 | 8 |
| NPJC6794 | | −2.06 | | | | | | 3.69 | 17.42 |

-continued

| | | | | | | | | |
|---|---|---|---|---|---|---|---|---|
| NPJC6794 | | 0.71 | | | | | 1.67 | −3.33 |
| NPJC6794 | | | | | | 43.59 | 0 | −9.17 |
| NPJC6794 | | −13.15 | | | | | | |
| NPJC6794 | | −2.06 | | | | | −13.42 | −7.83 |
| NPJC6794 | | | | | | 41.98 | −26.67 | −9.17 |
| NPJC6794 | | 1.47 | | | | | −4 | −0.5 |
| NPJC6794 | | | | | | 32.95 | −26.67 | −14.17 |
| NPJC6794 | | | | | | | 5 | 18 |
| NPJC6794 | | −2.94 | | | | | 6 | 17 |
| NPJC6794 | | −2.94 | | | | | 13.5 | 22 |
| NPJC6794 | | −2.94 | | | | | −9 | −0.5 |
| NPJC6794 | | −1.47 | | | | | 1 | −8 |
| NPJC6794 | | 21.08 | | | | | −3.49 | 25.19 |
| NPJC6794 | −13.33 | 6.9 | 1.13 | 0.5 | 41.56 | 17.57 | −14.79 | −2.04 |
| NPJC6794 | | −2.94 | | | | | −21.5 | 2 |
| NPJC6794 | | −1.32 | | | | | 8.41 | 4.36 |
| NPJC6794 | 16.67 | −1.31 | 0.23 | 0.42 | 2.44 | −19.4 | −17.5 | −8.89 |
| NPJC6794 | | 2.94 | | | | | 6 | 17 |
| NPJC6794 | | −10.38 | | | | | 21.67 | 11.67 |
| NPJC6794 | | −2.94 | | | | | −1.5 | 9.5 |
| NPJC6794 | | | | | | | | |
| NPJC6794 | | −2.03 | | | | | | |
| NPJC6794 | | 4.86 | | | 41.33 | 46.17 | 21.25 | 22.92 |
| NPJC6794 | | −2.77 | | | | | | |
| NPJC6794 | −2.86 | 1.42 | | 1 | 18 | 26.29 | 0.49 | 19.35 |
| NPJC6794 | | | | | | | 1.48 | 4.12 |
| NPJC6794 | | −2.77 | | | | | | |
| NPJC6794 | | | | | | | −6.14 | −18.7 |
| NPJC6794 | | | | | | | 5 | 12.14 |
| NPJC6794 | | 0 | | | | | 1 | −3 |
| NPJC6794 | | | | | | | | |
| NPJC6794 | | 65.55 | | | −7.67 | −2.83 | 13.75 | 37.92 |
| NPJC6794 | | 0.15 | | | | | 0.89 | 6 |
| NPJC6794 | | −0.4 | | | | | −3.33 | 1.67 |
| NPJC6794 | | | | | | | 5.17 | 6.5 |
| NPJC6794 | | | | | | | −8.64 | 10.31 |
| NPJC6794 | | 1.4 | | | | | | |
| NPJC6794 | 6.07 | −0.15 | 0.44 | 0.06 | −4.63 | 1.1 | 5.35 | 9.41 |
| NPJC6794 | | −0.2 | | −0.64 | 30.31 | 41.35 | −3.31 | 1.83 |
| NPJC6794 | | −0.59 | | | | | −6.65 | 4.28 |
| NPJC6794 | | 1 | | | | | | |
| NPJC6794 | | −1.72 | | | | | −1.5 | 9.5 |
| NPJC6794 | −8.33 | 7.44 | 0.88 | −0.95 | 20.05 | 7.4 | 4.17 | 0.33 |
| NPJC6794 | | −2.94 | | | | | −4 | 9.5 |
| NPJC6794 | | −0.65 | | | | | | |
| NPJC6794 | | −1.47 | | | | | −1.5 | 12 |
| NPJC6794 | | −2.94 | | | | | −16.5 | −5.5 |
| NPJC6794 | | | | | | 92.17 | −16.67 | 5.83 |
| NPJC6794 | | | | | | | 14.29 | 16.43 |
| NPJC6794 | −3.33 | 5.33 | 0.88 | −0.5 | −19.1 | 3.07 | 2.5 | 22 |
| NPJC6794 | | 0.17 | | | | | | |
| NPJC6794 | | 0 | | | | | | |
| NPJC6794 | | | | | | | | |
| NPJC6794 | 17.14 | 2.34 | 0.14 | 1 | 18 | 14.29 | 1.45 | 7.67 |
| NPJC6794 | 1.57 | −9.18 | 0.02 | 0.37 | 7.48 | 6.27 | −1.35 | 0.53 |
| NPJC6794 | | | | | | | | |
| NPJC6794 | −1.67 | −1.92 | 0.06 | −0.33 | 65.89 | 67.39 | 3.15 | 5.6 |
| NPJC6794 | | 0 | | | | | | |
| NPJC6794 | | −0.59 | | | | | −1.7 | −2.36 |
| NPJC6794 | | 0.47 | | | | | 3.5 | 9.5 |
| NPJC6794 | | 3.82 | | | | | 1.69 | 13.59 |
| NPJC6794 | −2.86 | −0.53 | −0.86 | 1 | 61.34 | 14.29 | −1.06 | 3.08 |
| NPJC6794 | | −1.81 | | | | | 2.81 | −7.42 |
| NPJC6794 | | −1.08 | | | | | 16.67 | 16.67 |
| NPJC6794 | 6.67 | −0.78 | 0.63 | 0.39 | 53.63 | 56.39 | 14.58 | 10.19 |
| NPJC6794 | | | | | | | −1.02 | −4.69 |
| NPJC6794 | | | | | | | −14.95 | −12.31 |
| NPJC6794 | | | | | | | 2.79 | 12.89 |
| NPJC6794 | | | | | | | −1.02 | 12.93 |
| NPJC6794 | | | | | | | −11.14 | −3.5 |
| NPJC6794 | | | | | | | | |
| NPJC6794 | 13.57 | −3.65 | 0.12 | 0.86 | 58.13 | 47.85 | 4.29 | 9.79 |
| NPJC6794 | | −3.33 | | | | | | |
| NPJC6794 | | | | | | | | |
| NPJC6794 | −2.86 | 0.98 | | 1 | 18 | 26.29 | 2.34 | 20.51 |
| NPJC6794 | | −2.21 | | | | | | |
| NPJC6794 | | 0 | | | | | | |
| NPJC6794 | | | | | | | | |
| NPJC6794 | | | | | | | | |

-continued

| | | | | | |
|---|---|---|---|---|---|
| NPJC6794 | 0 | | | | |
| NPJC6794 | 0 | | | | |
| NPJC6794 | | | | | |
| NPJC6794 | −9.9 | | | 11.67 | 6.67 |
| NPJC6794 | −2.55 | | | −12.5 | −2 |
| NPJC6794 | −4.02 | | | −12.5 | −4.5 |
| NPJC6794 | | | | | |
| NPJC6794 | −1.72 | | | −0.83 | 8.33 |
| NPJC6794 | 0.15 | | | 4.59 | 14.91 |
| NPJC6794 | −2.55 | | | 7.5 | 8 |
| NPJC6794 | 3.33 | | | −16 | 1 |
| NPJC6794 | | 58.48 | | −26.67 | 0.83 |
| NPJC6794 | 0 | | | −15.84 | −26.76 |
| NPJC6794 | 6.13 | −7.67 | −2.83 | −1.25 | 7.92 |
| NPJC6794 | −2.55 | | | −7.5 | 15.5 |
| NPJC6794 | | | | | |
| NPJC6794 | | | | | |
| NPJC6794 | | 73.95 | | −16.67 | 5.83 |
| NPJC6794 | −2.55 | | | −2.5 | 23 |
| NPJC6794 | 7.75 | | | −12.5 | −4.5 |
| NPJC6794 | −4.02 | | | −5 | −2 |
| NPJC6794 | −7.38 | | | 6.67 | 6.67 |
| NPJC6794 | −3.89 | | | 1.67 | 16.67 |
| NPJC6794 | −9.55 | | | −8.33 | −3.33 |
| NPJC6794 | | | | | |
| NPJC6794 | −1.08 | | | −5 | 13 |
| NPJC6794 | −4.69 | | | −11.85 | 7.72 |
| NPJC6794 | −2.55 | | | −17.5 | 3 |
| NPJC6794 | 12.19 | | | 6.67 | 1.67 |
| NPJC6794 | −3.76 | | | −8.46 | −5.93 |
| NPJC6794 | | | | −19.95 | −12.27 |
| NPJC6794 | −2.77 | | | | |
| NPJC6794 | −0.98 | | | −3.33 | −8.33 |
| NPJC6794 | | | | −24.89 | −24.38 |
| NPJC6794 | −0.24 | | | −2.5 | 5.83 |
| NPJC6794 | −1.32 | | | −1.7 | 5.97 |
| NPJC6794 | −2.55 | | | 14.24 | −12.5 |
| NPJC6794 | | | | −9.96 | 4.45 |
| NPJC6794 | | | | −1.52 | 15.4 |
| NPJC6794 | | | | 0.82 | 13.06 |
| NPJC6794 | | | | −9.38 | 1.59 |
| NPJC6794 | | | | −13.03 | 6.63 |
| NPJC6794 | | | | 7.17 | 14.25 |
| NPJC6794 | | | | −14.18 | −14.68 |
| NPJC6794 | | | | −18.27 | 7.81 |
| NPJC6794 | | | | 0.12 | 24.56 |
| NPJC6794 | | | | −4.91 | 16.2 |
| NPJC6794 | | | | −0.73 | 7.81 |
| NPJC6794 | | | | −14.09 | 15.3 |
| NPJC6794 | | | | 0.94 | 7.78 |
| NPJC6794 | | | | −22.48 | 0.3 |
| NPJC6794 | | | | −5.76 | 20.4 |
| NPJC6794 | | | | −2.95 | 16.79 |
| NPJC6794 | | | | −14.96 | 14.53 |
| NPJC6794 | | | | −12.42 | 10.35 |
| NPJC6794 | | | | −5.53 | 18.02 |
| NPJC6794 | −3.53 | | | −4.61 | −3.48 |
| NPJC6794 | | | | 3.48 | 6.14 |
| NPJC6794 | | | | −6.64 | 21.83 |
| NPJC6794 | | | | −24.38 | 9.13 |
| NPJC6794 | | | | −5.76 | 7.78 |
| NPJC6794 | | | | 0.78 | −0.91 |
| NPJC6794 | | | | 4.3 | 11.17 |
| NPJC6794 | | | | −4.04 | 9.48 |
| NPJC6794 | | | | −9.22 | 16.83 |
| NPJC6794 | | | | −1.72 | 6.67 |
| NPJC6794 | | | | −19.96 | −8.09 |
| NPJC6794 | | | | −6.52 | 18.68 |
| NPJC6794 | | | | −5.68 | 4.5 |
| NPJC6794 | | | | −2.37 | 17.02 |
| NPJC6794 | | | | −10.53 | 6.63 |
| NPJC6794 | | | | −7.4 | 14.53 |
| NPJC6794 | | | | −5.49 | 4.17 |
| NPJC6794 | | | | −2.4 | 11.99 |
| NPJC6794 | | | | −14.09 | −12.27 |
| NPJC6794 | | | | −14.3 | 6.67 |
| NPJC6794 | | | | 2.66 | 22.04 |
| NPJC6794 | | | | −2.99 | 14.25 |
| NPJC6794 | | | | −10.61 | 10.48 |
| NPJC6794 | | | | −7.45 | 15.35 |

-continued

| | | | | | | | | |
|---|---|---|---|---|---|---|---|---|
| NPJC6794 | | | | | | | −1.55 | 7.81 |
| NPJC6794 | | | | | | | −20.84 | 17.07 |
| NPJC6794 | | −2.03 | | | | | | |
| NPJC6794 | 7.14 | 1.03 | | 1 | −33.5 | −12.71 | −5.89 | −0.25 |
| NPJC6794 | | −0.27 | | | | | | |
| NPJC6794 | | −1.18 | | | | | −5.03 | 8.51 |
| NPJC6794 | | −2.77 | | | | | | |
| NPJC6794 | | −0.37 | | | | | | |
| NPJC6794 | −3.33 | −2.02 | 0.23 | −0.88 | 36.38 | 32.35 | 0.05 | 15.38 |
| NPJC6794 | −2.86 | 1.92 | −0.86 | 1 | 6 | 14.29 | 8.03 | 12.49 |
| NPJC6794 | | −1.32 | | | | | 0.02 | −4 |
| NPJC6794 | 10 | −1.26 | −0.22 | 0.32 | 0.25 | 14.42 | 25.93 | 14.45 |
| NPJC6794 | | −1.1 | | | | | | |
| NPJC6794 | | −0.74 | | | | | | |
| NPJC6794 | −3.33 | 0.43 | 0.63 | −2.5 | −19.1 | −9.43 | −7.5 | −1.33 |
| NPJC6794 | | | | | | | | |
| NPJC6794 | | −0.37 | | | | | | |
| NPJC6794 | | −2.77 | | | | | | |
| NPJC6794 | 1.67 | 1.56 | −0.57 | 0.04 | 16.13 | 12.1 | −9.58 | −3.87 |
| NPJC6794 | 1.67 | 7.35 | 0.38 | −1.5 | 59.4 | 42.57 | 0.83 | 12 |
| NPJC6794 | | 1.4 | | | | | | |
| NPJC6794 | | −2.77 | | | | | | |
| NPJC6794 | | 0.56 | | | | | | |
| NPJC6794 | | −0.74 | | | | | | |
| NPJC6794 | | −1.1 | | | | | | |
| NPJC6794 | −3.33 | −0.74 | 0.83 | −1.5 | 34.9 | 30.07 | 0.83 | 12 |
| NPJC6794 | −2.86 | 1.86 | 0.14 | 1 | 18 | 14.29 | 3.63 | 6.16 |
| NPJC6794 | 7.14 | 1.67 | −0.86 | 1 | 59 | 53.29 | 6.63 | 26.87 |
| NPJC6794 | −2.86 | −0.12 | −1.86 | 1 | 72 | 65.79 | 3.3 | 19.5 |
| NPJC6794 | 8.57 | −1.31 | −0.23 | 0.49 | 16.13 | 27.6 | 2.86 | 6.6 |
| NPJC6794 | | 0.15 | | | | | −4.19 | 6.93 |
| NPJC6794 | | −2.94 | | | | | −9.32 | −1.54 |
| NPJC6794 | | | | | | | −25.11 | −8.23 |
| NPJC6794 | | −1.32 | | | | | −10.09 | −2.39 |
| NPJC6794 | | −2.94 | | | | | −6.73 | −9.93 |
| NPJC6794 | | 0.15 | | | | | −5.91 | 6.87 |
| NPJC6794 | | −1.32 | | | | | 4.2 | 10.21 |
| NPJC6794 | | −3.92 | | | | | 15.56 | 12.49 |
| NPJC6794 | | 0.15 | | | | | −0.85 | 7.67 |
| NPJC6794 | | −1.32 | | | | | −5.06 | 8.51 |
| NPJC6794 | | 1.96 | | | | | −2.22 | 6.14 |
| NPJC6794 | | −1.32 | | | | | 1.66 | 16.11 |
| NPJC6794 | | −1.32 | | | | | −22.63 | 2.67 |
| NPJC6794 | | 0.88 | | | | | 4.17 | −3.23 |
| NPJC6794 | | −1.32 | | | | | −4.21 | 0.13 |
| NPJC6794 | | −0.59 | | | | | −6.7 | −0.61 |
| NPJC6794 | | 0.15 | | | | | −5.06 | 11.05 |
| NPJC6794 | | −13.41 | | | | | 14.92 | 26.03 |
| NPJC6794 | | −1.65 | | | | | −16.83 | 13.34 |
| NPJC6794 | | −11.94 | | | | | 3.49 | 24.76 |
| NPJC6794 | | −10.36 | | | | | 21.67 | 21.67 |
| NPJC6794 | | −7.85 | | | | | 11.67 | 11.67 |
| NPJC6794 | | −7.32 | | | | | −3.33 | 6.67 |
| NPJC6794 | | −9.35 | | | | | 6.67 | 6.67 |
| NPJC6794 | | −0.59 | | | | | 5.02 | 7.67 |
| NPJC6794 | | 1.47 | | | | | 0.87 | 13.54 |
| NPJC6794 | | −2.06 | | | | | −19.29 | −6.57 |
| NPJC6794 | | 0.15 | | | | | −9.19 | −9.03 |
| NPJC6794 | | −1.32 | | | | | −16.78 | −4.03 |
| NPJC6794 | | −2.06 | | | | | −6.7 | 3.51 |
| NPJC6794 | | 0.15 | | | | | −0.77 | −4 |
| NPJC6794 | | −0.59 | | | | | −15.09 | 3.54 |
| NPJC6794 | | −2.06 | | | | | −0.77 | 14.44 |
| NPJC6794 | | 1.47 | | | | | 2.59 | 8.59 |
| NPJC6794 | | 1.62 | | | | | −4.21 | 3.57 |
| NPJC6794 | | −9.55 | | | | | 1.67 | 1.67 |
| NPJC6794 | | −7.91 | | | | | 6.67 | 21.67 |
| NPJC6794 | | −3.53 | | | | | −10.46 | 2.37 |
| NPJC6794 | | −1.47 | 0.67 | −0.38 | 5.77 | 10.66 | −3.73 | 13.24 |
| NPJC6794 | | −3.92 | | | | | 10.48 | 16.3 |
| NPJC6794 | | −2.79 | | | | | 10.47 | 5.7 |
| NPJC6794 | | −2.06 | | | | | −1.23 | −7.71 |
| NPJC6794 | | −3.24 | | | | | 2.08 | −4.33 |
| NPJC6794 | | −10.85 | | | | | 6.67 | −8.33 |
| NPJC6794 | | −8.1 | | | | | −3.33 | 6.67 |
| NPJC6794 | | −10.85 | | | | | 6.67 | 11.67 |
| NPJC6794 | | 3.18 | | | | | 6.67 | 11.67 |
| NPJC6794 | | −5.4 | | | | | −3.33 | −3.33 |
| NPJC6794 | | −8.36 | | | | | 6.67 | −3.33 |
| NPJC6794 | | 1.62 | | | | | −7.1 | −4.33 |

-continued

| | | | | | | | |
|---|---|---|---|---|---|---|---|
| NPJC6794 | | −1.32 | | | | 17.19 | 0.65 |
| NPJC6794 | | 1.62 | | | | −7.15 | −8.53 |
| NPJC6794 | | −11.94 | | | | −1.59 | 18.42 |
| NPJC6794 | | 2.65 | | | | −7.92 | −6.02 |
| NPJC6794 | | 10 | | | | −2.95 | −1.84 |
| NPJC6794 | | 1.47 | | | | −1.67 | 0.97 |
| NPJC6794 | | 6.76 | | | | 0.02 | 1.85 |
| NPJC6794 | | −2.06 | | | | −9.24 | 5.15 |
| NPJC6794 | | −6.88 | | | | −8.33 | −8.33 |
| NPJC6794 | | −9.89 | | | | −3.33 | 1.67 |
| NPJC6794 | | −9.34 | | | | −3.33 | 6.67 |
| NPJC6794 | | −9.38 | | | | 16.67 | 1.67 |
| NPJC6794 | | −10.36 | | | | 16.67 | 11.67 |
| NPJC6794 | | 1.31 | | | | 11.67 | 6.67 |
| NPJC6794 | | −2.06 | | | | −12.6 | −0.69 |
| NPJC6794 | | −8.8 | | | | 1.67 | −3.33 |
| NPJC6794 | | −2.94 | | | | 4.2 | −0.72 |
| NPJC6794 | | −5.95 | | | | 21.67 | 11.67 |
| NPJC6794 | | −9.84 | | | | 1.67 | 11.67 |
| NPJC6794 | | −1.31 | | | | 16.67 | 16.67 |
| NPJC6794 | | −10.85 | | | | 16.67 | 11.67 |
| NPJC6794 | | −3.01 | | | | 6.67 | 6.67 |
| NPJC6794 | | 1.4 | | | | −3.33 | 6.67 |
| NPJC6794 | | 3.25 | | | | 11.67 | 21.67 |
| NPJC6794 | | 14.59 | | | | 1.67 | −3.33 |
| NPJC6794 | | −2.79 | | | | 10.49 | −0.09 |
| NPJC6794 | | −0.29 | | | | 15.88 | 8 |
| NPJC6794 | | −2.79 | | | | 14.67 | 26.63 |
| NPJC6794 | | −3.53 | | | | 4.9 | 11.09 |
| NPJC6794 | | −3.53 | | | | 5.44 | 6.52 |
| NPJC6794 | | −2.79 | | | | 7.13 | 4.06 |
| NPJC6794 | | −2.79 | | | | −7.13 | −2.69 |
| NPJC6794 | | −2.06 | | | | −1.33 | −0.99 |
| NPJC6794 | | −3.53 | | | | 3.72 | 21.63 |
| NPJC6794 | | −2.06 | | | | −3.79 | −1.45 |
| NPJC6794 | | 6.8 | | | | 6.67 | −8.33 |
| NPJC6794 | | −10.36 | | | | 1.67 | 1.67 |
| NPJC6794 | | 2 | | | | 1.67 | −13.33 |
| NPJC6794 | | 1.72 | | | 17.33 | 22.17 | 6.25 | 25.42 |
| NPJC6794 | | 9.07 | | | −7.67 | 22.17 | 16.25 | 20.42 |
| NPJC6794 | | 0.25 | | | −7.67 | −2.83 | 3.75 | 17.92 |
| NPJC6794 | | −2.3 | | | | −3.33 | 16.67 |
| NPJC6794 | | −1.02 | | | 17.33 | 22.17 | 6.25 | 10.42 |
| NPJC6794 | | −1.23 | | | 66.33 | 71.17 | 13.75 | 17.92 |
| NPJC6794 | | −1.31 | | | | −27.51 | −4.66 |
| NPJC6794 | | 0.53 | | | | 6.67 | 11.67 |
| NPJC6794 | | −2.76 | −1.17 | −0.37 | 24.5 | 15.33 | −13.03 | 3.48 |
| NPJC6794 | | −1.23 | | | −7.67 | −2.83 | −1.25 | 25.42 |
| NPJC6794 | | 1.72 | | | −7.67 | −2.83 | 8.75 | 22.92 |
| NPJC6794 | | −3.7 | 1.83 | −1.65 | 9 | −0.17 | −8.8 | 14.41 |
| NPJC6794 | | −0.2 | | | 17.33 | 22.17 | 3.75 | 22.92 |
| NPJC6794 | | 10.54 | | | 41.33 | 71.17 | 11.25 | 37.92 |
| NPJC6794 | | 14.95 | | | −36.67 | −31.83 | 13.75 | 30.42 |
| NPJC6794 | | −4.71 | | | | −3.03 | 7.34 |
| NPJC6794 | | 1.72 | | | −7.67 | −2.83 | 13.75 | 32.92 |
| NPJC6794 | | −4.17 | | | −7.67 | 22.17 | 8.75 | 2.92 |
| NPJC6794 | | −1.23 | | | −36.67 | −31.83 | −6.25 | 5.42 |
| NPJC6794 | | 0.25 | | | −7.67 | −2.83 | 3.75 | 17.92 |
| NPJC6794 | | −5.08 | | | | 1.67 | 11.67 |
| NPJC6794 | | −0.08 | −0.17 | −1.2 | 71.83 | 62 | 9.45 | 28.3 |
| NPJC6794 | 5 | −13.09 | 1.17 | −2.06 | 0 | 5.17 | −15.83 | −8.33 |
| NPJC6794 | 15 | −2.68 | −0.39 | 0.65 | −14.75 | 0.42 | 3.25 | −2.52 |
| NPJC6794 | | −3.86 | −0.17 | −1.03 | 68.11 | 53.28 | −8.29 | 6.26 |
| NPJC6794 | | 14.95 | | | 66.33 | 71.17 | 23.75 | 32.92 |
| NPJC6794 | 0 | 0.18 | 0.1 | 0.28 | 29.75 | 44.42 | 9.95 | 15.28 |
| NPJC6794 | 25 | 11.87 | −0.3 | 0.48 | 0.25 | 28.92 | 12.08 | 18.79 |
| NPJC6794 | | | | | | | | |
| NPJC6794 | | −7.87 | | | | 1.67 | 16.67 |
| NPJC6794 | 15 | −1.31 | 0.44 | −0.02 | −14.75 | 0.42 | 11.4 | 6.89 |
| NPJC6794 | | 20.83 | | | 17.33 | 22.17 | −3.75 | 10.42 |
| NPJC6794 | 0 | −2.63 | −0.39 | 0.75 | 0.25 | 14.42 | 20.91 | 27.64 |
| NPJC6794 | | −3.5 | | | | 6.67 | 1.67 |
| NPJC6794 | | 7.6 | | | 17.33 | 22.17 | 21.25 | 35.42 |
| NPJC6794 | | 9.07 | | | 41.33 | 71.17 | 11.25 | 20.42 |
| NPJC6794 | | 4.66 | | | 17.33 | 22.17 | 11.25 | 20.42 |
| NPJC6794 | | 9.07 | | | 41.33 | 46.17 | 11.25 | 20.42 |
| NPJC6794 | | 14.95 | | | 41.33 | 46.17 | 8.75 | 30.42 |
| NPJC6794 | | 2.26 | | | −7.67 | −2.83 | 11.25 | 17.92 |
| NPJC6794 | | 4.66 | | | 17.33 | 22.17 | 13.75 | 32.92 |
| NPJC6794 | | 12.01 | | | −36.67 | −2.83 | 11.25 | 30.42 |

-continued

| | | | | | | | | |
|---|---|---|---|---|---|---|---|---|
| NPJC6794 | | −0.2 | | | 41.33 | 71.17 | 21.25 | 27.92 |
| NPJC6794 | | 1.72 | | | 41.33 | 46.17 | 13.75 | 42.92 |
| NPJC6794 | | 0.25 | | | 41.33 | 71.17 | 23.75 | 30.42 |
| NPJC6794 | | 3.19 | | −3.86 | 59.74 | 46.01 | −4.01 | 9.81 |
| NPJC6794 | | | | | 85.17 | | −11.67 | −9.17 |
| NPJC6794 | | −1.11 | | | | | 12 | 25.5 |
| NPJC6794 | | | | | 34.98 | | −16.67 | −9.17 |
| NPJC6794 | | −2.77 | | | | | | |
| NPJC6794 | | | | | | | −3.93 | 6.21 |
| XR = | 2.85 | −0.79 | 0.15 | −0.07 | 25 | 22.58 | −1.23 | 7.86 |
| XH = | 3.64 | −0.65 | 0.11 | −0.15 | 22.41 | 22.37 | −0.89 | 7.72 |
| XT = | 2.94 | 1.36 | 0.26 | −0.25 | 22.99 | 19.91 | −0.73 | 8.94 |

XR = GCA ESTIMATE: WEIGHTED BY EXPT
XH = GCA ESTIMATE: WEIGHTED BY PARENT2
XT = SAME AS XH, BUT USING ONLY THOSE PARENT2 WITH TWO YEARS OF DATA

The Paired Hybrid Comparison Data Table A shows the inbred NPJC6794 in hybrid combination, as Hybrid 1, in comparison with another hybrid, which is adapted for the same region of the Corn Belt.

PAIRED HYBRID COMPARISON DATA TABLE A

| Hybrid | Yield | Moist | TWT | PCTERL | PCTSL | PCTPUSH | PLTLRL | PCTDE |
|---|---|---|---|---|---|---|---|---|
| Hybrid1 w/NPJC6794 | 177.9 | 18.6 | 55.7 | 3 | 3.2 | 23.9 | 0.9 | 0.1 |
| Hybrid2 | 182.3 | 18.2 | 55.8 | 3.7 | 0.6 | 30.9 | 0.6 | 0 |
| # Expts | 326 | 326 | 211 | 12 | 173 | 57 | 54 | 29 |
| Diff | 4.3 | 0.4 | 0.1 | 0.7 | 2.6 | 7 | 0.4 | 0.1 |
| Prob | 0.003*** | 0.003*** | 0.417 | 0.116 | 0.000*** | 0.062* | 0.467 | 0.076* |

| Hybrid | Stand | PCTSG | PCTGS | PctBarren | Emerge | Vigor | HUS50 |
|---|---|---|---|---|---|---|---|
| Hybrid1 w/NPJC6794 | 231.4 | 24.7 | 3.4 | | 3.1 | 3.2 | 1360 |
| Hybrid2 | 232.6 | 13.2 | 2 | | 3.6 | 3.7 | 1361 |
| # Expts | 324 | 17 | 22 | | 85 | 108 | 13 |
| Diff | 1.2 | 11.5 | 1.4 | | 0.5 | 0.5 | 0.9 |
| Prob | 0.306 | 0.007*** | 0.182 | | 0.000*** | 0.001*** | 0.931 |

| Hybrid | HUP50 | Pltht | Earht |
|---|---|---|---|
| Hybrid1 w/NPJC6794 | 1373 | 258.2 | 111.4 |
| Hybrid2 | 1365 | 223.8 | 95.5 |
| # Expts | 13 | 13 | 13 |
| Diff | 7.4 | 34.3 | 15.8 |
| Prob | 0.466 | 0.000*** | 0.009*** |

*.05 < Prob <= .10
**.01 < Prob <= .05
***.00 < Prob <= .01

| Hybrid | Yield | Moist | TWT | PCTERL | PCTSL | PCTPUSH | PLTLRL | PCTDE |
|---|---|---|---|---|---|---|---|---|
| Hybrid1 w/NPJC6794 | 179.1 | 18.3 | 55.8 | 6.8 | 3.3 | 30.5 | 0.7 | 0.1 |
| Hybrid3 | 184 | 17.1 | 57.9 | 31.1 | 1.4 | 20 | 1.8 | 0.1 |
| # Expts | 207 | 207 | 145 | 10 | 116 | 33 | 33 | 16 |
| Diff | 4.8 | 1.2 | 2.1 | 24.3 | 1.9 | 10.4 | 1 | 0 |
| Prob | 0.003*** | 0.000*** | 0.000*** | 0.016** | 0.000*** | 0.047** | 0.336 | 0.761 |

| Hybrid | Stand | PCTSG | PCTGS | PctBarren | Emerge | Vigor | HUS50 |
|---|---|---|---|---|---|---|---|
| Hybrid1 w/NPJC6794 | 245.5 | 23.3 | 3.2 | | 3.2 | 3 | 1383 |
| Hybrid3 | 251.7 | 22.6 | 3 | | 3.3 | 3.3 | 1389 |
| # Expts | 207 | 12 | 18 | | 59 | 58 | 8 |
| Diff | 6.2 | 0.8 | 0.2 | | 0.1 | 0.3 | 6.3 |
| Prob | 0.000*** | 0.836 | 0.834 | | 0.441 | 0.011** | 0.577 |

-continued

| Hybrid | HUP50 | Pltht | Earht |
|---|---|---|---|
| Hybrid1 w/NPJC6794 | 1396 | 250.9 | 102.8 |
| Hybrid3 | 1393 | 248.7 | 125.8 |
| # Expts | 8 | 8 | 8 |
| Diff | 3.5 | 2.2 | 23 |
| Prob | 0.635 | 0.423 | 0.027** |

The Yield by Environment Response Table shows the yield response of Hybrid 1 w/NPJC6794 as a parent in comparison with two other hybrids and the plants in the environment around it at the same location.

Yield By Environment Response Table
Research Plots

| Hybrid | Error | # Plots | 75 | 100 | 125 | 150 | 175 | 200 |
|---|---|---|---|---|---|---|---|---|
| Hybrid1 w/NPJC6794 | 21.5 | 142 | 75 | 100 | 126 | 151 | 177 | 202 |
| Hybrid2 | 24.2 | 11641 | 85 | 108 | 131 | 154 | 178 | 201 |
| Hybrid1 w/NPJC6794 | 21.5 | 142 | 75 | 100 | 126 | 151 | 177 | 202 |
| Hybrid3 | 21.3 | 4289 | 82 | 105 | 129 | 152 | 176 | 200 |

Accordingly, the present invention has been described with some degree of particularity directed to the embodiment of the present invention. It should be appreciated, though that the present invention is defined by the following claims construed in light of the prior art so that modifications or changes may be made to the embodiment of the present invention without departing from the inventive concepts contained herein.

The invention claimed is:

1. A seed of the maize variety NPJC6794, representative seed sample deposited under ATCC Accession Number PTA-12400.

2. A maize plant NPJC6794, representative seed sample of said NPJC6794 plant having been deposited under ATCC Accession Number PTA-12400.

3. A plant part of the plant of claim 2.

4. The plant part of claim 3, wherein said part is a pollen grain, a protoplast, a cell, a tassel, an anther or an ovule.

5. A maize seed comprising the plant part of claim 3, said plant part is a cell.

6. A process for producing maize seed, said process comprising crossing the plant of maize line NPJC6794 according to claim 2 with a different maize plant.

7. A maize plant or plant part produced by growing the maize seed obtained from the process of claim 6.

8. A method for producing maize seed comprising growing the plant of claim 2 until seed is produced and harvesting the seed.

9. A seed produced by the method of claim 8.

10. A process of introducing a heritable trait into a plant of maize variety NPJC6794 comprising: (a) crossing NPJC6794 plants grown from NPJC6794 seeds, representative seed sample deposited under ATCC Accession Number PTA-12400, with plants of another maize plant that comprise a desired trait to produce hybrid progeny plants, (b) selecting hybrid progeny plants that have the desired trait to produce selected hybrid progeny plants; (c) crossing the selected hybrid progeny plants with the NPJC6794 plants to produce backcross progeny plants; (d) selecting for backcross progeny plants that have the desired trait to produce selected backcross progeny plants; and (e) repeating steps (c) and (d) at least three or more times to produce backcross progeny plants that comprise the desired trait and all of the physiological and morphological characteristics of maize inbred plant NPJC6794 when grown in the same environmental conditions.

11. A plant produced by the process of claim 10.

12. A maize plant produced by the process of claim 10, wherein the desired trait is selected from the group consisting of waxy starch, male sterility or restoration of male fertility, modified carbohydrate metabolism, modified protein metabolism and modified fatty acid metabolism, altered starch, thermotolerant amylase, herbicide resistance; insect resistance, nematode resistance, bacterial disease resistance, fungal disease resistance, and viral disease resistance.

13. The maize plant of claim 12, wherein said trait is conferred by a transgene.

14. The maize plant of claim 13, wherein the transgene confers a trait selected from the group consisting of herbicide resistance; insect resistance, nematode resistance; bacterial resistance, fungal resistance, viral disease resistance; waxy starch; altered starch, thermotolerant amylase, male sterility, restoration of male fertility, modified carbohydrate metabolism, modified protein metabolism and modified fatty acid metabolism.

15. A method of producing a maize plant derived from the inbred plant NPJC6794, the method comprising the steps of (a) growing a progeny plant wherein one parent of said progeny plant is the plant of claim 2; (b) crossing the progeny plant with itself or a different plant to produce a seed of a subsequent generation; (c) growing a progeny plant of the subsequent generation from said seed and crossing the progeny plant of the subsequent generation with itself or another plant; and (d) repeating step (c) for an additional generation to produce a maize plant derived from the inbred plant NPJC6794.

16. A method for developing a maize plant in a maize plant breeding program, comprising applying plant breeding techniques comprising recurrent selection, backcrossing, pedigree breeding, marker enhanced selection, haploid/double haploid production, or transformation to the maize plant of claim 2, or its parts, wherein application of said techniques results in development of a maize plant.

17. A method of producing a commodity plant product comprising growing the plant from the seed of claim 9, or a part thereof, and producing said commodity plant product comprising protein concentrate, protein isolate, starch, meal, flour or oil therefrom.

18. A maize seed produced by crossing the plant of claim 2 with a different maize plant.

* * * * *